US012728284B2

(12) United States Patent
Novosad et al.

(10) Patent No.: US 12,728,284 B2
(45) Date of Patent: Sep. 8, 2026

(54) JOINTLY TRAINED MACHINE LEARNING MODELS FOR AUTOMATIC CONTOURING IN RADIOTHERAPY APPLICATIONS

(71) Applicant: Elekta LTD., Montreal (CA)

(72) Inventors: Philip P. Novosad, Montreal (CA); Silvain Beriault, Longueuil (CA)

(73) Assignee: Elekta LTD., Montreal (CA)

( * ) Notice: Subject to any disclaimer, the term of this patent is extended or adjusted under 35 U.S.C. 154(b) by 410 days.

(21) Appl. No.: 18/187,122

(22) Filed: Mar. 21, 2023

(65) Prior Publication Data

US 2023/0377721 A1 Nov. 23, 2023

Related U.S. Application Data

(60) Provisional application No. 63/364,995, filed on May 19, 2022.

(51) Int. Cl.

| | |
|---|---|
| ***A61N 5/10*** | (2006.01) |
| ***G06N 3/045*** | (2023.01) |
| ***G06N 20/00*** | (2019.01) |
| ***G06T 7/00*** | (2017.01) |
| ***G06T 7/11*** | (2017.01) |

(52) U.S. Cl.

CPC ........... *A61N 5/1031* (2013.01); *G06N 3/045* (2023.01); *G06N 20/00* (2019.01); *G06T 7/0012* (2013.01); *G06T 7/11* (2017.01); *G06T 2207/20084* (2013.01)

(58) Field of Classification Search

CPC ......... A61N 5/1031; A61N 2005/1041; G06N 3/045; G06N 3/0464; G06N 3/09; G06N 20/00; G06T 7/0012; G06T 7/11; G06T 2207/10116; G06T 2207/20081; G06T 2207/20084; G16H 20/40

See application file for complete search history.

(56) References Cited

U.S. PATENT DOCUMENTS

| | | | |
|---|---|---|---|
| 9,697,602 B1 | 7/2017 | Zhou et al. | |
| 10,970,829 B2 * | 4/2021 | Zheng ................. | G06V 10/774 |
| 11,232,319 B2 | 1/2022 | Udupa et al. | |

(Continued)

OTHER PUBLICATIONS

Ma et al. “A discriminative learning based approach for automated nasopharyngeal carcinoma segmentation leveraging multi-modality similarity metric learning.” 2018 IEEE 15th International Symposium on Biomedical Imaging (ISBI 2018). IEEE, 2018. (Year: 2018).*

(Continued)

*Primary Examiner* — Katrina R Fujita

(74) *Attorney, Agent, or Firm* — Schwegman Lundberg & Woessner, P.A.

(57) ABSTRACT

Joint training techniques to train multiple models across clinical datasets for automatic contouring. Rather than using separate deep neural networks that are trained independently for each different dataset (e.g., a different image contrast or anatomy), joint training can be used to train multiple models simultaneously across clinical datasets for automatic contouring. By taking advantage of commonalities between two or more datasets, the techniques effectively take advantage of data that would otherwise be considered irrelevant to the task—allowing the user to train more performant models while requiring less training data per dataset.

23 Claims, 12 Drawing Sheets

1300

1302 Obtain the image of the subject

1304 Select, based on an image parameter, a previously trained machine learning model, where the previously trained machine learning model was jointly trained 1306 Apply the previously trained machine learning model to the image of the subject to generate a machine learning model output 1308 Contour, without user intervention and based on the machine learning model output, one or more anatomical structures of the image 1310 Process the one or more contoured anatomical structures to generate the radiotherapy treatment plan

(56) References Cited

U.S. PATENT DOCUMENTS

| | | | | |
|---|---|---|---|---|
| 2017/0103287 | A1 | 4/2017 | Han | |
| 2019/0066281 | A1* | 2/2019 | Zheng | G06N 3/047 |
| 2019/0261945 | A1* | 8/2019 | Funka-Lea | A61B 8/0883 |
| 2019/0370965 | A1 | 12/2019 | Lay et al. | |
| 2020/0185079 | A1* | 6/2020 | Yan | G06F 16/2365 |
| 2021/0065360 | A1 | 3/2021 | Laaksonen et al. | |
| 2021/0192279 | A1* | 6/2021 | Laaksonen | G16H 30/20 |
| 2021/0304402 | A1 | 9/2021 | Morgas et al. | |
| 2022/0180523 | A1 | 6/2022 | Novosad et al. | |
| 2022/0180524 | A1 | 6/2022 | Novosad et al. | |
| 2023/0018833 | A1* | 1/2023 | Das | G16H 50/70 |
| 2023/0131675 | A1* | 4/2023 | Kunz | G06N 20/20 382/128 |

OTHER PUBLICATIONS

Elmahdy et al. "Joint registration and segmentation via multi-task learning for adaptive radiotherapy of prostate cancer." IEEE Access 9 (2021): 95551-95568. (Year: 2021).*

Tomar et al. "Self-attentive spatial adaptive normalization for cross-modality domain adaptation." IEEE transactions on medical imaging 40.10 (2021): 2926-2938. (Year: 2021).*

Bilen, Hakan, et al., "Universal representations: The missing link between faces, text, planktons, and cat breeds", arXiv:1701.07275v1 [cs.CV], (Jan. 25, 2017), 10 pgs.

Chang, Woong-Gi, et al., "Domain-Specific Batch Normalization for Unsupervised Domain Adaptation", arXiv:1906.03950v1 [cs.LG], (May 27, 2019), 9 pgs.

Li, Yanghao, et al., "Revisiting Batch Normalization for Practical Domain Adaptation", arXiv:1603.04779v4 [cs.CV], (Nov. 8, 2016), 12 pgs.

Qi, Dou, et al., "Unpaired Multi-modal Segmentation via Knowledge Distillation", IEEE Transactions on Medical Imaging vol. 39, Issue: 7, (Jan. 6, 2020), 11 pgs.

Ronneberger, Olaf, et al., "U-Net: Convolutional Networks for Biomedical Image Segmentation", arXiv:1505.04597v1 [cs.CV], (May 18, 2015), 8 pgs.

Valindria, Vanya, et al., "Multi-Modal Learning from Unpaired Images: Application to Multi-Organ Segmentation in CT and MRI", 2018 IEEE Winter Conference on Applications of Computer Vision (WACV), (May 7, 2018), 10 pgs.

Zhang, Zhengxin, et al., "Road Extraction by Deep Residual U-Net", IEEE Geoscience and Remote Sensing Letters vol. 15, Issue: 5, (May 2018), 5 pgs.

"European Application Serial No. 23171940.2, Extended European Search Report mailed Sep. 28, 2023", 8 pgs.

"European Application Serial No. 23171940.2, Response filed May 11, 2024 to Extended European Search Report mailed Sep. 28, 2023", 14 pgs.

* cited by examiner

JOINTLY TRAINED MACHINE LEARNING MODELS FOR AUTOMATIC CONTOURING IN RADIOTHERAPY APPLICATIONS

CLAIM OF PRIORITY

This application claims the benefit of priority of U.S. Provisional Patent Application Ser. No. 63/364,995, titled "JOINT TRAINING OF DEEP NEURAL NETWORKS ACROSS CLINICAL DATASETS FOR AUTOMATIC CONTOURING IN RADIOTHERAPY APPLICATIONS" to Philip P. Novosad and Silvain Bériault, filed on May 19, 2022, the entire contents of which being incorporated herein by reference.

TECHNICAL FIELD

Embodiments of the present disclosure pertain generally to image segmentation in radiotherapy treatment.

BACKGROUND

Radiation therapy (or "radiotherapy") may be used to treat cancers or other ailments in mammalian (e.g., human and animal) tissue. One such radiotherapy technique involves irradiation with a Gamma Knife®, whereby a patient is irradiated by a large number of low-intensity gamma ray beams that converge with high intensity and high precision at a target (e.g., a tumor). In another embodiment, radiotherapy is provided using a linear accelerator, whereby a tumor is irradiated by high-energy particles (e.g., electrons, protons, ions, high-energy photons, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs). Radiation is termed "prescribed" because a physician orders a predefined amount of radiation to the tumor and surrounding organs similar to a prescription for medicine. Generally, ionizing radiation in the form of a collimated beam is directed from an external radiation source toward a patient but the radiation may also come from radioactive seeds located in the tumor.

A specified or selectable beam energy can be used, such as for delivering a diagnostic energy level range or a therapeutic energy level range. Modulation of a radiation beam can be provided by one or more attenuators or collimators (e.g., a multi-leaf collimator (MLC)). The intensity and shape of the radiation beam can be adjusted by collimation to avoid damaging healthy tissue (e.g., OARs) adjacent to the targeted tissue by conforming the projected beam to a profile of the targeted tissue.

The treatment planning procedure may include using a three-dimensional (3D) image of the patient to identify a target region (e.g., the tumor) and to identify critical organs near the tumor. Creation of a treatment plan can be a time-consuming process where a planner tries to comply with various treatment objectives or constraints (e.g., dose volume histogram (DVH), overlap volume histogram (OVH)), taking into account their individual importance (e.g., weighting) in order to produce a treatment plan that is clinically acceptable. This task can be a time-consuming trial-and-error process that is complicated by the various OARs because as the number of OARs increases (e.g., up to thirteen for a head-and-neck treatment), so does the complexity of the process. OARs distant from a tumor may be easily spared from radiation, while OARs close to or overlapping a target tumor may be difficult to spare.

Traditionally, for each patient, the initial treatment plan can be generated in an "offline" manner. The treatment plan can be developed well before radiation therapy is delivered, such as using one or more medical imaging techniques.

Imaging information can include, for example, images from X-rays, computed tomography (CT), nuclear magnetic resonance (MR), positron emission tomography (PET), single-photon emission computed tomography (SPECT), or ultrasound. A health care provider, such as a physician, may use 3D imaging information indicative of the patient anatomy to identify one or more target tumors along with the OARs near the tumor(s). The health care provider can delineate the target tumor that is to receive a prescribed radiation dose using a manual technique, and the health care provider can similarly delineate nearby tissue, such as organs, at risk of damage from the radiation treatment. Alternatively, or additionally, an automated tool (e.g., ABAS provided by Elekta AB, Sweden) can be used to assist in identifying or delineating the target tumor and organs at risk. A radiation therapy treatment plan ("treatment plan") can then be created using an optimization technique based on clinical and dosimetric objectives and constraints (e.g., the maximum, minimum, and fraction of dose of radiation to a fraction of the tumor volume ("95% of target shall receive no less than 100% of prescribed dose"), and like measures for the critical organs). The optimized plan is comprised of numerical parameters that specify the direction, cross-sectional shape, and intensity of each radiation beam.

The treatment plan can then be later executed by positioning the patient in the treatment machine and delivering the prescribed radiation therapy directed by the optimized plan parameters. The radiation therapy treatment plan can include dose "fractioning," whereby a sequence of radiation treatments is provided over a predetermined period of time (e.g., 30-45 daily fractions), with each treatment including a specified fraction of a total prescribed dose. However, during treatment, the position of the patient and the position of the target tumor in relation to the treatment machine (e.g., linear accelerator—"linac") is very important in order to ensure the target tumor and not healthy tissue is irradiated.

Since most patients receive more than one fraction of radiation as part of a course of therapy, and because the anatomy may change (deform) between these fractions, it is not straightforward to sum the doses delivered during the individual fractions so the physician can accurately gauge how the treatment is proceeding relative to the original intent as defined by the prescription.

Overview

This disclosure describes using joint training techniques to train multiple models across clinical datasets for automatic contouring. Rather than using separate deep neural networks that are trained independently for each different dataset (e.g., a different image contrast or anatomy), the present inventors recognized that joint training can be used to train multiple models simultaneously across clinical datasets for automatic contouring. By taking advantage of commonalities between two or more datasets, the techniques of this disclosure effectively take advantage of data that would otherwise be considered irrelevant to the task—allowing the user to train more performant models while requiring less training data per dataset.

In some aspects, this disclosure is directed to a computer-implemented method for generating a radiotherapy treatment plan for a subject including training processing circuitry to automatically contour an image depicting an anatomy of the subject, the method comprising: jointly training at least two machine learning models, wherein the at least two machine learning models are configured to share at least one parameter, and wherein, when trained, the machine learning models are configured to automatically contour images for radiotherapy treatment.

In some aspects, this disclosure is directed to a computer-implemented method for generating a radiotherapy treatment plan for a subject including automatically contouring an image depicting an anatomy of the subject, the method comprising: obtaining the image of the subject; selecting, based on an image parameter, a previously trained machine learning model, wherein the previously trained machine learning model was jointly trained; applying the previously trained machine learning model to the image of the subject to generate a machine learning model output; contouring, without user intervention and based on the machine learning model output, one or more anatomical structures of the image; and processing the one or more contoured anatomical structures to generate the radiotherapy treatment plan.

In some aspects, this disclosure is directed to a radiotherapy system for generating a radiotherapy treatment plan for a patient including automatically contouring an image depicting an anatomy of the subject, the radiotherapy system comprising: a radiation therapy device configured to deliver a dose of radiation to an anatomical region of interest; and a processor configured to: obtain the image of the subject; select, based on an image parameter, a previously trained machine learning model, wherein the previously trained machine learning model was jointly trained; apply the previously trained machine learning model to the image of the subject to generate a machine learning model output; contour, without user intervention and based on the machine learning model output, one or more anatomical structures of the image; and process the one or more contoured anatomical structures to generate the radiotherapy treatment plan.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
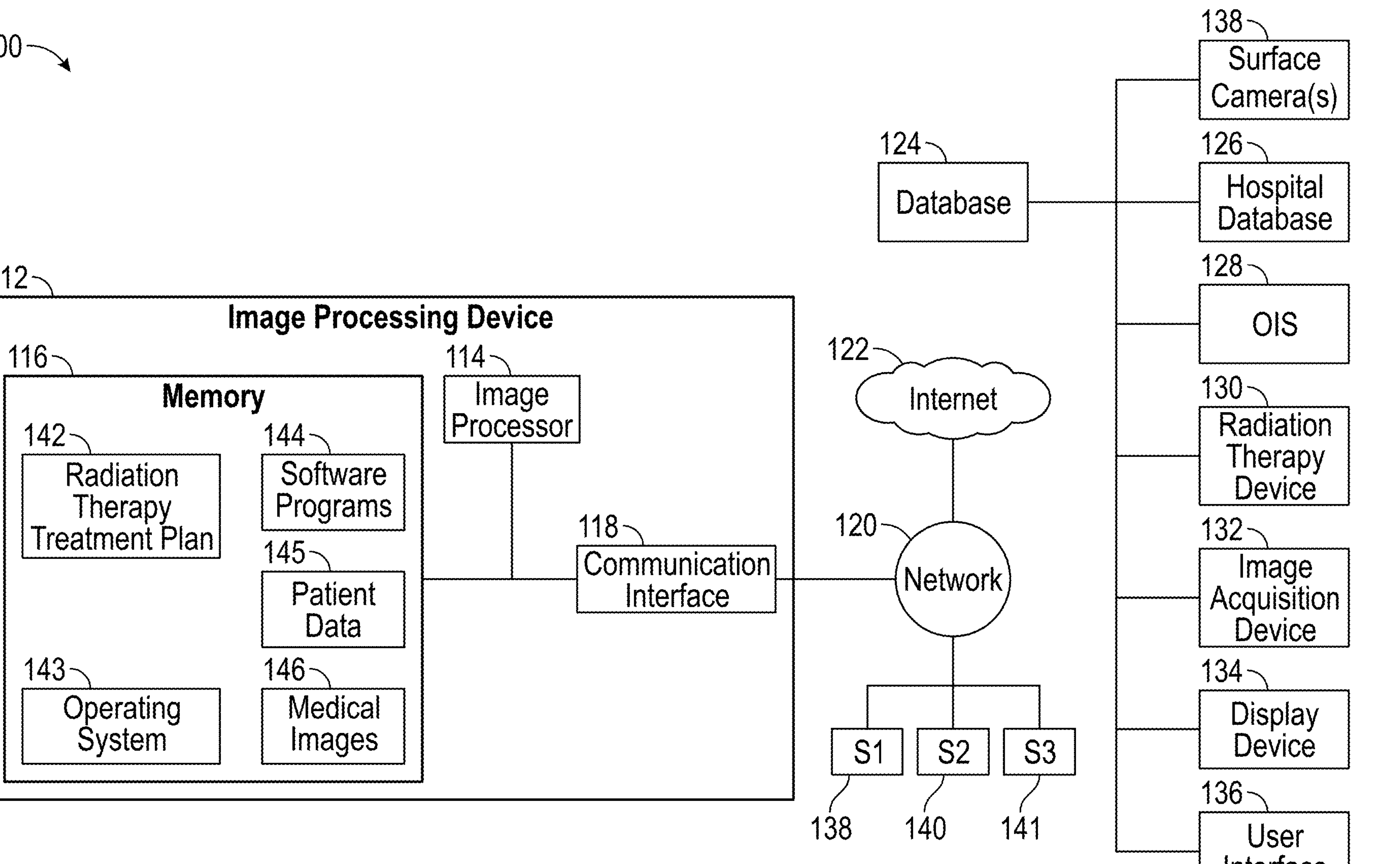
FIG. 1 illustrates an example of a radiotherapy system, according to some embodiments of the present disclosure.

In the following detailed description, reference is made to the accompanying drawings which form a part hereof, and which is shown by way of illustration-specific embodiments in which the present disclosure may be practiced. These embodiments, which are also referred to herein as "examples," are described in sufficient detail to enable those skilled in the art to practice the disclosure, and it is to be understood that the embodiments may be combined, or that other embodiments may be utilized, and that structural, logical, and electrical changes may be made without departing from the scope of the present disclosure. The following detailed description is, therefore, not be taken in a limiting sense, and the scope of the present disclosure is defined by the appended claims and their equivalents.

Segmentation (or "contouring") of organs-at-risk (OARs) is an important step in radiotherapy treatment planning. Although manual contouring is the gold standard approach for segmentation, it is a highly time-consuming task and is subject to both inter- and intra-rater variability. Consequently, there is a tension between obtaining accurate contours on the one hand and retaining a high clinical throughput on the other. This tension is particularly evident in adaptive workflows (e.g., as supported by the Elekta Unity MR-Linac), which, optimally, utilizes a new set of accurate contours at each treatment fraction (on the MRI of the day).

In recent years, commercial solutions for automatic contouring based on machine learning have become increasingly common, due to their capacity to produce highly accurate and reliable contours in a fraction of the time required by a manual rater. However, the present inventors have recognized that, for optimal performance, such models require vast training sets (consisting of many pairs of images and training labels) from which to learn. As such, the present inventors have recognized that the development of accurate machine learning models therefore bears a considerable cost associated with the collection and curation of large sets of training data.

This disclosure describes using joint training techniques to train multiple models across clinical datasets for automatic contouring. Rather than using separate deep neural networks that are trained independently for each different dataset (e.g., a different image contrast or anatomy), the present inventors recognized that joint training can be used to train multiple models simultaneously across clinical datasets for automatic contouring. By taking advantage of commonalities between two or more datasets, the techniques of this disclosure effectively take advantage of data that would otherwise be considered irrelevant to the task—allowing the user to train more performant models while requiring less training data per dataset.

As an example, one can jointly train male and female pelvis models, effectively doubling the number of training examples for any OAR that is common to both training datasets (e.g., bony anatomy, bladder, and rectum). This approach can also be used to jointly training various (similar) models to better cope with differences in anatomy due to pre-treatment ablative surgeries (e.g., prostatectomy, hysterectomy, etc.). This approach can also be used to jointly train various (similar) models to better cope with differences in imaging contrast in MRI (e.g. auto-contouring the same anatomical region on T1-weighted versus T2-weighted MR images). This approach can also be used to jointly train various similar models to better cope with difference in image quality (e.g., training a basic model with a limited set of structures on lower quality images vs training a premium model with an enhanced set of structures on higher quality images).

FIG. 1 illustrates an example of a radiotherapy system 100 for providing radiation therapy to a patient. The radiotherapy system 100 includes an image processing device 112. The image processing device 112 may be connected to a network 120. The network 120 may be connected to the Internet 122. The network 120 may connect the image processing device 112 with one or more of a database 124, a hospital database 126, an oncology information system (OIS) 128, a radiation therapy device 130, an image acquisition device 132, a display device 134, a user interface 136, and one or more surface cameras 138, such as surface cameras 138A-138C in FIG. 2A and/or surface camera 138D in FIG. 2B. Examples of surface cameras 138 may include those manufactured by C-Rad, VisionRT, and Varian HumediQ. The surface camera(s) 138 (e.g., one or more 2D or 3D cameras) may be used to acquire real-time images of the surface of a patient's body (e.g., the patient's skin) while medical images are being acquired. For Gamma Knife® mask treatments, an IR camera registers movements of markers fixed on the nose of the patient. Because the surface imaging is taken at the same time as the medical imaging, the surface imaging may provide a more accurate definition of the location of the boundaries of the patient's body while the medical imaging was taken. The image processing device 112 may be configured to generate radiation therapy treatment plans 142 to be used by the radiation therapy device 130.

The image processing device 112 may include a memory device 116, an image processor 114, and a communication interface 118. The memory device 116 may store computer-executable instructions, such as an operating system 143, radiation therapy treatment plans 142 (e.g., original treatment plans, adapted treatment plans and the like), software programs 144 (e.g., artificial intelligence, deep learning, neural networks, radiotherapy treatment plan software), and any other computer-executable instructions to be executed by the image processor 114.

In one embodiment, the software programs 144 may convert medical images of one format (e.g., MRI) to another format (e.g., CT) by producing synthetic images, such as pseudo-CT images. For instance, the software programs 144 may include image processing programs to train a predictive model for converting a medical image 146 in one modality (e.g., an MRI image) into a synthetic image of a different modality (e.g., a pseudo-CT image); alternatively, the trained predictive model may convert a CT image into an MM image.

In another embodiment, the software programs 144 may register the patient image (e.g., a CT image or an MR image) with that patient's dose distribution (also represented as an image) so that corresponding image voxels and dose voxels are associated appropriately by the network.

In yet another embodiment, the software programs 144 may substitute functions of the patient images or processed versions of the images that emphasize some aspect of the image information. Such functions might emphasize edges or differences in voxel textures, or any other structural aspect useful to neural network learning.

In another embodiment, the software programs 144 may substitute functions of the dose distribution that emphasize some aspect of the dose information. Such functions might emphasize steep gradients around the target or any other structural aspect useful to neural network learning. The memory device 116 may store data, including medical images 146, patient data 145, and other data required to create and implement a radiation therapy treatment plan 142.

In yet another embodiment, the software programs 144 may generate a structural estimate (e.g., a 3D model of the region of interest) using an iterative image reconstruction process. The structural estimate may be or include an X-ray attenuation map that represents a 3D model of a region of interest. The structural estimate may be used to estimate or simulate X-ray measurements to be compared with real X-ray measurements for updating the structural estimate. Specifically, the software programs 144 may access a current structural estimate of the region of interest and generate a first simulated X-ray measurement based on the current structural estimate of the region of interest.

A simulated X-ray measurement, as referred to herein, represents the expected output of an X-ray detector element when an X-ray source projects one or more X-ray beams through the region of interest towards the X-ray detector element. The simulated X-ray measurement may provide an expected image output that is to be received from the X-ray detector element.

The software programs 144 may receive a first real X-ray measurement from a CBCT system (or other CT imaging system, such as an enclosed gantry helical multi-slice CT with a curved detector or tomotherapy system) and generate an update to the current structural estimate of the region of interest as a function of the first simulated X-ray measurement and the first real X-ray measurement. A real X-ray measurement, as referred to herein, is an actual output that is received from a CBCT system (or other CT imaging system, such as an enclosed gantry helical multi-slice CT with a curved detector or tomotherapy system) that represents the amount of signal generated by X-rays in the detector along different directions, such as in an image form.

The update may be generated invariant on (independent of) the current structural estimate. The structural estimate may be used to control one or more radiotherapy treatment parameters by recalculating dose, adjusting one or more radiotherapy treatment machine parameters, or generating a display of the structural estimate on a graphical user interface.

In addition to the memory device 116 storing the software programs 144, it is contemplated that software programs 144 may be stored on a removable computer medium, such as a hard drive, a computer disk, a CD-ROM, a DVD, a HD, a Blu-Ray DVD, USB flash drive, a SD card, a memory stick, or any other suitable medium; and the software programs 144 when downloaded to image processing device 112 may be executed by image processor 114.

The processor 114 may be communicatively coupled to the memory device 116, and the processor 114 may be configured to execute computer-executable instructions stored thereon. The processor 114 may send or receive medical images 146 to memory device 116. For example, the processor 114 may receive medical images 146 from the image acquisition device 132 via the communication interface 118 and network 120 to be stored in memory device 116. The processor 114 may also send medical images 146 stored in memory device 116 via the communication interface 118 to the network 120 be either stored in database 124 or the hospital database 126.

Further, the processor 114 may utilize software programs 144 (e.g., a treatment planning software) along with the medical images 146 and patient data 145 to create the radiation therapy treatment plan 142. Medical images 146 may include information such as imaging data associated with a patient anatomical region, organ, or volume of interest segmentation data. Patient data 145 may include information such as (1) functional organ modeling data (e.g., serial versus parallel organs, appropriate dose response models, etc.); (2) radiation dosage data (e.g., DVH information); or (3) other clinical information about the patient and course of treatment (e.g., other surgeries, chemotherapy, previous radiotherapy, etc.).

In addition, the processor 114 may utilize software programs to generate intermediate data such as updated parameters to be used, for example, by a machine learning model, such as a neural network model; or generate intermediate 2D or 3D images, which may then subsequently be stored in memory device 116. The processor 114 may subsequently transmit the executable radiation therapy treatment plan 142 via the communication interface 118 to the network 120 to the radiation therapy device 130, where the radiation therapy plan will be used to treat a patient with radiation. In addition, the processor 114 may execute software programs 144 to implement functions such as image conversion, image segmentation, deep learning, neural networks, and artificial intelligence. For instance, the processor 114 may execute software programs 144 that train or contour a medical image; such software programs 144 when executed may train a boundary detector or utilize a shape dictionary.

The processor 114 may be a processing device, including one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application-specific integrated circuit (ASIC), a field programmable gate array (FPGA), a digital signal processor (DSP), a System on a Chip (SoC), or the like. As would be appreciated by those skilled in the art, in some embodiments, the processor 114 may be a special-purpose processor rather than a general-purpose processor. The processor 114 may include one or more known processing devices, such as a microprocessor from the Pentium™, Core™, Xeon™, or Itanium® family manufactured by Intel™, the Turion™, Athlon™, Sempron™, Opteron™ FX™ Phenom™ family manufactured by AMD™, or any of various processors manufactured by Sun Microsystems. The processor 114 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 114 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor (for example, a multi-core design or a plurality of processors each having a multi-core design). The processor 114 may execute sequences of computer program instructions, stored in memory device 116, to perform various operations, processes, methods that will be explained in greater detail below.

The memory device 116 may store medical images 146. In some embodiments, the medical images 146 may include one or more MRI images (e.g., 2D MM, 3D MRI, 2D streaming MM, four-dimensional (4D) MRI, 4D volumetric MRI, 4D cine MRI, etc.), functional MM images (e.g., fMRI, DCE-MRI, diffusion MRI), CT images (e.g., 2D CT, cone beam CT, 3D CT, 4D CT), ultrasound images (e.g., 2D ultrasound, 3D ultrasound, 4D ultrasound), one or more projection images representing views of an anatomy depicted in the MM, synthetic CT (pseudo-CT), and/or CT images at different angles of a gantry relative to a patient axis, PET images, X-ray images, fluoroscopic images, radiotherapy portal images, SPECT images, computer generated synthetic images (e.g., pseudo-CT images), aperture images, graphical aperture image representations of MLC leaf positions at different gantry angles, and the like. Further, the medical images 146 may also include medical image data, for instance, training images, ground truth images, contoured images, and dose images. In an embodiment, the medical images 146 may be received from the image acquisition device 132. Accordingly, image acquisition device 132 may include an MRI imaging device, a Megavolt (MV) imaging device, a CT imaging device, a CBCT imaging device, a PET imaging device, an ultrasound imaging device, a fluoroscopic device, a SPECT imaging device, an integrated linac and MRI imaging device, an integrated linac and CT imaging device, an integrated linac and CBCT imaging device, or other medical imaging devices for obtaining the medical images of the patient. The medical images 146 may be received and stored in any type of data or any type of format that the image processing device 112 may use to perform operations consistent with the disclosed embodiments.

MRI images may be acquired using various pulse sequences. Two of the basic pulse sequences include longitudinal (T1) and transverse (T2) relaxation time sequences that generate T1-weighted images and T2-weighted images, respectively. MRI contrast agents are a group of contrast media used to improve the visibility of internal body structures by increasing contrast between normal tissues and abnormal tissues in MRI. MRI contrast agents alter the T1 (longitudinal) and T2 (transverse) relaxation times of tissues and body cavities where they are present and, depending on the image weighting, may result in a higher or lower signal. T1 MRI contrast agents produce the "bright" contrast in a T1-weighted image, whereas T2 MRI contrast agents create "dark" contrast effects.

The memory device 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a CD-ROM, a DVD or other optical storage, a cassette tape, other magnetic storage device, or any other non-transitory medium that may be used to store information including image, data, or computer-executable instructions (e.g., stored in any format) capable of being accessed by the processor 114, or any other type of computer device. The computer program instructions may be accessed by the processor 114, read from the ROM, or any other suitable memory location, and loaded into the RAM for execution by the processor 114. For example, the memory device 116 may store one or more software applications. Software applications stored in the memory device 116 may include, for example, an operating system 143 for common computer systems as well as for software-controlled devices. Further, the memory device 116 may store an entire software application, or only a part of a software application, that is executable by the processor 114. For example, the memory device 116 may store one or more radiation therapy treatment plans 142.

The image processing device 112 may communicate with the network 120 via the communication interface 118, which may be communicatively coupled to the processor 114 and the memory device 116. The communication interface 118 may provide communication connections between the image processing device 112 and radiotherapy system 100 components (e.g., permitting the exchange of data with external devices). For instance, the communication interface 118 may, in some embodiments, have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 118 may include one or more digital and/or analog communication devices that permit image processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3 (141). Systems S1, S2, and S3 may be identical to image processing device 112 or may be different systems. In some embodiments, one or more systems in network 120 may form a distributed computing/simulation environment that collaboratively performs the embodiments described herein. In some embodiments, one or more systems 51, S2, and S3 may include a CT scanner that obtains CT images (e.g., medical images 146). In addition, network 120 may be connected to Internet 122 to communicate with servers and clients that reside remotely on the internet.

Therefore, network 120 may allow data transmission between the image processing device 112 and a number of various other systems and devices, such as the OIS 128, the radiation therapy device 130, and the image acquisition device 132. Further, data generated by the OIS 128 and/or the image acquisition device 132 may be stored in the memory device 116, the database 124, and/or the hospital database 126. The data may be transmitted/received via network 120, through communication interface 118 in order to be accessed by the processor 114, as required.

The image processing device 112 may communicate with database 124 through network 120 to send/receive a plurality of various types of data stored on database 124. For example, database 124 may include machine data (control points) that includes information associated with a radiation therapy device 130, image acquisition device 132, or other machines relevant to radiotherapy. Machine data information may include control points, such as radiation beam size, arc placement, beam on and off time duration, machine parameters, segments, MLC configuration, gantry speed, MRI pulse sequence, and the like. Database 124 may be a storage device and may be equipped with appropriate database administration software programs. One skilled in the art would appreciate that database 124 may include a plurality of devices located either in a central or a distributed manner.

In some embodiments, database 124 may include a processor-readable storage medium. While the processor-readable storage medium in an embodiment may be a single medium, the term "processor-readable storage medium" should be taken to include a single medium or multiple media (e.g., a centralized or distributed database, and/or associated caches and servers) that store the one or more sets of computer-executable instructions or data. The term "processor-readable storage medium" shall also be taken to include any medium that is capable of storing or encoding a set of instructions for execution by a processor and that cause the processor to perform any one or more of the methodologies of the present disclosure. The term "processor-readable storage medium" shall accordingly be taken to include, but not be limited to, solid-state memories and optical and magnetic media. For example, the processor-readable storage medium may be one or more volatile, non-transitory, or non-volatile tangible computer-readable media.

Image processor 114 may communicate with database 124 to read images into memory device 116 or store images from memory device 116 to database 124. For example, the database 124 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DICOM) data, projection images, graphical aperture images, etc.) that the database 124 received from image acquisition device 132. Database 124 may store data to be used by the image processor 114 when executing software program 144 or when creating radiation therapy treatment plans 142. Database 124 may store the data produced by the trained machine learning mode, such as a neural network including the network parameters constituting the model learned by the network and the resulting estimated data. As referred to herein, "estimate" or "estimated" may be used interchangeably with "predict" or "predicted" and should be understood to have the same meaning. The image processing device 112 may receive the imaging data, such as a medical image 146 (e.g., 2D MRI slice images, CT images, 2D Fluoroscopy images, X-ray images, 3DMRI images, 4D MRI images, projection images, graphical aperture images, image contours, etc.) from the database 124, the radiation therapy device 130 (e.g., a linac or an MR-linac), and/or the image acquisition device 132 to generate a treatment plan 142. The radiation therapy device 130 may provide linac based treatments such as volumetric-modulated arc therapy (VMAT) or intensity modulated radiation therapy (IMRT), for example.

In an embodiment, the radiotherapy system 100 may include an image acquisition device 132 that may acquire medical images (e.g., MRI images, 3D MRI, 2D streaming MRI, 4D volumetric MRI, CT images, cone-Beam CT, PET images, functional MRI images (e.g., fMRI, DCE-MRI, and diffusion MRI), X-ray images, fluoroscopic image, ultrasound images, radiotherapy portal images, SPECT images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the image acquisition device 132 may be stored within database 124 as either imaging data and/or test data. By way of example, the images acquired by the image acquisition device 132 may be also stored by the image processing device 112 as medical images 146 in memory device 116.

In an embodiment, for example, the image acquisition device 132 may be integrated with the radiation therapy device 130 as a single apparatus (e.g., an MR-linac). Such an MR-linac may be used, for example, to determine a location of a target organ or a target tumor in the patient, so as to direct radiation therapy accurately according to the radiation therapy treatment plan 142 to a predetermined target.

The image acquisition device 132 may be configured to acquire one or more images, such as including spatial imaging data, of the patient's anatomy for a region of interest (e.g., a target organ, a target tumor, or both). Each image, typically a 2D image or slice, may include one or more parameters (e.g., a 2D slice thickness, an orientation, and a location, etc.). In an embodiment, the image acquisition device 132 may acquire a 2D slice in any orientation. For example, an orientation of the 2D slice may include a sagittal orientation, a coronal orientation, or an axial orientation. The processor 114 may adjust one or more parameters, such as the thickness and/or orientation of the 2D slice, to include the target organ and/or target tumor. In an embodiment, 2D slices may be determined from information such as a 3D MRI volume. Such 2D slices may be acquired by the image acquisition device 132 in "real-time" while a patient is undergoing radiation therapy treatment, for example, when using the radiation therapy device 130, with "real-time" meaning acquiring the data in at least milliseconds or less. The image acquisition device 132 may be configured to acquire 3D spatial imaging data.

The image processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as control points including beam angles, gantry angles, beam intensity, dose-histogram-volume information, the number of radiation beams to be used during therapy, the dose per beam, and the like.

The image processor 114 may generate the radiation therapy treatment plan 142 by using software programs 144 such as treatment planning software (such as Leksell Gamma Plan® Monaco®, manufactured by Elekta, Sweden). In order to generate the radiation therapy treatment plans 142, the image processor 114 may communicate with the image acquisition device 132 (e.g., a CT device, an MM device, a PET device, an X-ray device, an ultrasound device, etc.) to access images of the patient and to delineate a target, such as a tumor, to generate contours of the images. In some embodiments, the delineation of one or more OARs, such as healthy tissue surrounding the tumor or in close proximity to the tumor, may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 100 may study the dose distribution not only in the target but also in the OAR.

In order to delineate a target organ or a target tumor from the OAR, medical images, such as MRI images, CT images, PET images, fMRI images, X-ray images, ultrasound images, radiotherapy portal images, SPECT images, and the like, of the patient undergoing radiotherapy may be obtained non-invasively by the image acquisition device 132 to reveal the internal structure of a body part. Based on the information from the medical images, a 3D structure of the relevant anatomical portion may be obtained and used to generate a contour of the image. Contours of the image may include data overlaid on top of the image that delineates one or more structures of the anatomy. In some cases, the contours may be files associated with respective images that specify the coordinates or 2D or 3D locations of various structures of the anatomy depicted in the images.

In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as Leksell Gamma Plan® manufactured by Elekta) or automatically (e.g., using a program such as the Atlas-based auto-segmentation software, ABAS™, manufactured by Elekta). In certain embodiments, the 3D structure of a target tumor or an OAR may be generated automatically by the treatment planning software.

After the target tumor and the OAR(s) have been located and delineated, a dosimetrist, physician, or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times.

During the inverse-planning process, the physician may define dose constraint parameters that set bounds on how much radiation an OAR may receive (e.g., defining full dose to the tumor target and zero dose to any OAR; defining dose received by at least 95% of the target tumor volume; defining that the spinal cord, brain stem, and optic structures receive ≤45 Gy, ≤55 Gy and <54 Gy, respectively). The result of inverse planning may constitute a radiation therapy treatment plan 142 that may be stored in memory device 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 112 may generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (e.g., projection images, graphical aperture images, contours, dosages, beam angles, etc.) treatment plans, a target, localizing a target and/or tracking a target, or any related information to the user. The user interface 136 may be a keyboard, a keypad, a touch screen, or any type of device that a user may use to input information to radiotherapy system 100. Alternatively, the display device 134 and the user interface 136 may be integrated into a device such as a tablet computer (e.g., Apple iPad®, Lenovo Thinkpad®, Samsung Galaxy®, etc.).

Furthermore, any and all components of the radiotherapy system 100 may be implemented as a virtual machine (e.g., VMWare, Hyper-V, and the like). For instance, a virtual machine may be software that functions as hardware. Therefore, a virtual machine may include at least one or more virtual processors, one or more virtual memories, and one or more virtual communication interfaces that together function as hardware. For example, the image processing device 112, the OIS 128, and the image acquisition device 132 could be implemented as a virtual machine. Given the processing power, memory, and computational capability available, the entire radiotherapy system 100 could be implemented as a virtual machine.

Using various techniques of this disclosure, a system, such as the radiotherapy system 100, may obtain an image of a subject scheduled to receive radiotherapy treatment and select, based on an image parameter, a previously trained machine learning model from a set of previously trained machine models where at least one previously trained machine learning model was jointly trained using various techniques of this disclosure. Image parameters may include, for example, whether the image is a T1-weighted MRI image or T2-weighted MRI image, whether the image is a T2-weighted MRI image (or T1-weighted MM image) having a long scan time (e.g., higher resolution and/or image quality) or a T2-weighted MRI image (or T1-weighted MRI image) having a short scan time (i.e. lower resolution and/or image quality), whether the image includes anatomy of a male subject or anatomy of a female subject, whether the image includes a subject having had ablative surgery (e.g. prostatectomy, hysterectomy, etc.) and the second type includes a subject not having had a ablative surgery. After selecting the previously trained machine learning model, the system 100 may apply the previously trained machine learning model to the image of the subject to generate a machine learning model output. The system 100 may then contour, without user intervention and based on the machine learning model output, one or more anatomical structures of the image. In some examples, the system 100 may process the one or more contoured anatomical structures to generate the radiotherapy treatment plan.

Rather than using separate deep neural networks that are trained independently for each different dataset representing different combinations of previously described image parameters (e.g., a different image contrast, such as with T1-weighted and T2-weighted images, or anatomy), joint training can be used to train multiple models across clinical datasets for automatic contouring. By taking advantage of commonalities shared between two or more datasets, the techniques of this disclosure effectively take advantage of data that would otherwise be considered irrelevant to the task—allowing the user to train more performant models while requiring less training samples per dataset.

Figure 2A:
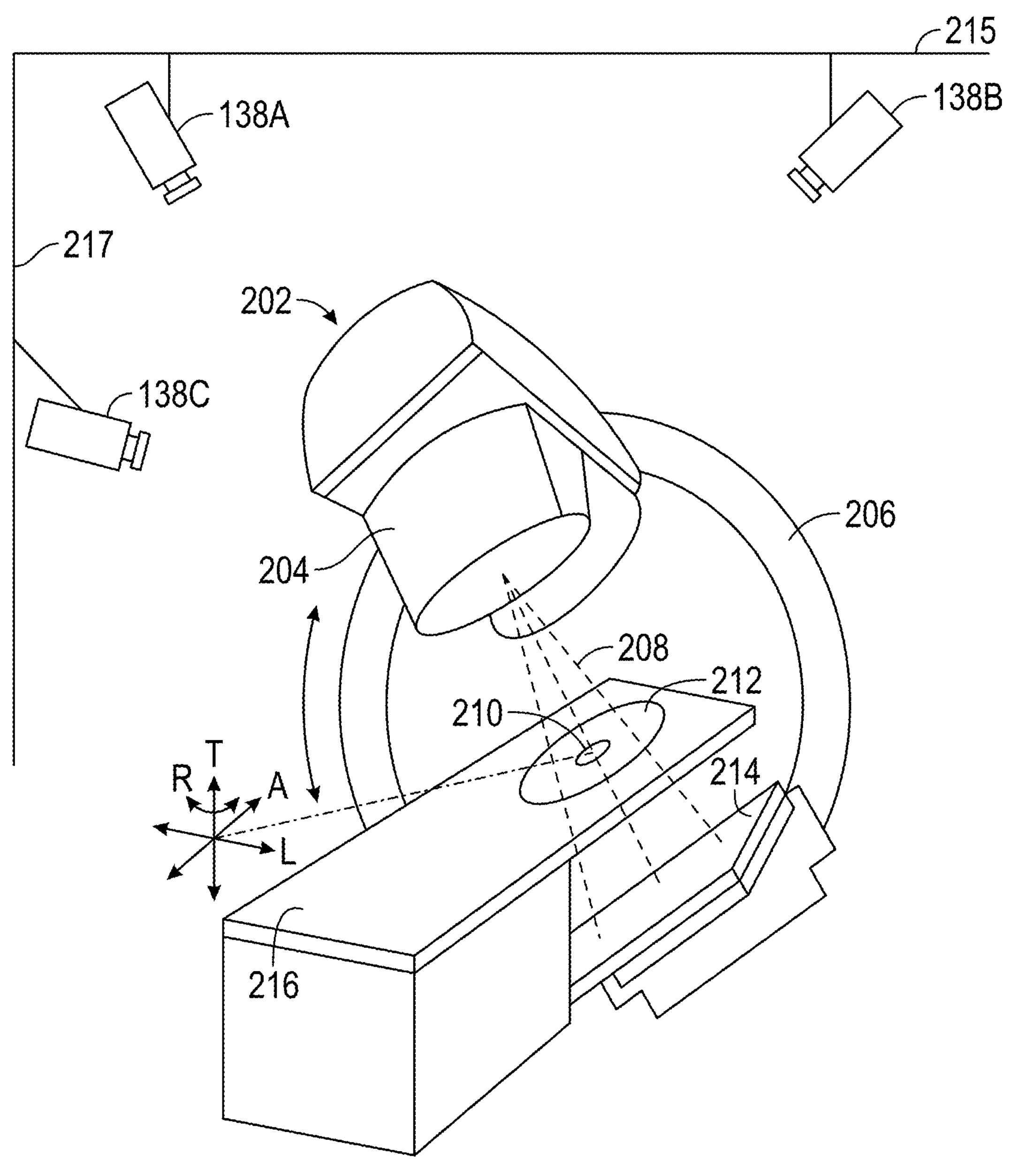
FIG. 2A illustrates an example a radiation therapy system that may include radiation therapy output configured to provide a therapy beam, according to some embodiments of the present disclosure.

FIG. 2A illustrates an example of a radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 may include one or more attenuators or collimators, such as an MLC as described in the illustrative embodiment of FIG. 5, below.

Referring back to FIG. 2A, a patient may be positioned in a region 212 and supported by the treatment couch 216 to receive a radiation therapy dose, according to a radiation therapy treatment plan. The radiation therapy output 204 may be mounted or attached to a gantry 206 or other mechanical support. One or more chassis motors (not shown) may rotate the gantry 206 and the radiation therapy output 204 around couch 216 when the couch 216 is inserted into the treatment area. In an embodiment, gantry 206 may be continuously rotatable around couch 216 when the couch 216 is inserted into the treatment area. In another embodiment, gantry 206 may rotate to a predetermined position when the couch 216 is inserted into the treatment area. For example, the gantry 206 may be configured to rotate the therapy output 204 around an axis ("A"). Both the couch 216 and the radiation therapy output 204 may be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch's 216 movements or rotations in order to properly position the patient in or out of the radiation beam 208 according to a radiation therapy treatment plan. Both the couch 216 and the gantry 206 are independently moveable from one another in multiple degrees of freedom, which allows the patient to be positioned such that the radiation beam 208 may precisely target the tumor. The MLC may be integrated and included within gantry 206 to deliver the radiation beam 208 of a certain shape.

The coordinate system (including axes A, T, and L) shown in FIG. 2A may have an origin located at an isocenter 210. The isocenter 210 may be defined as a location where the central axis of the radiation beam 208 intersects the origin of a coordinate axis, such as to deliver a prescribed radiation dose to a location on or within a patient. Alternatively, the isocenter 210 may be defined as a location where the central axis of the radiation beam 208 intersects the patient for various rotational positions of the radiation therapy output 204 as positioned by the gantry 206 around the axis A. As discussed herein, the gantry angle corresponds to the position of gantry 206 relative to axis A, although any other axis or combination of axes may be referenced and used to determine the gantry angle.

Gantry 206 may also have an attached imaging detector 214. The imaging detector 214 is preferably located opposite to the radiation source, and in an embodiment, the imaging detector 214 may be located within a field of the therapy beam 208.

The imaging detector 214 may be mounted on the gantry 206 (preferably opposite the radiation therapy output 204), such as to maintain alignment with the therapy beam 208. The imaging detector 214 rotates about the rotational axis as the gantry 206 rotates. In an embodiment, the imaging detector 214 may be a flat panel detector (e.g., a direct detector or a scintillator detector). In this manner, the imaging detector 214 may be used to monitor the therapy beam 208 or the imaging detector 214 may be used for imaging the patient's anatomy, such as portal imaging (e.g., to provide real X-ray measurements). The control circuitry of radiation therapy device 202 may be integrated within system 100 or remote from it.

In an illustrative embodiment, one or more of the couch 216, the therapy output 204, or the gantry 206 may be automatically positioned, and the therapy output 204 may establish the therapy beam 208 according to a specified dose for a particular therapy delivery instance. A sequence of therapy deliveries may be specified according to a radiation therapy treatment plan, such as using one or more different orientations or locations of the gantry 206, couch 216, or therapy output 204. The therapy deliveries may occur sequentially, but may intersect in a desired therapy locus on or within the patient, such as at the isocenter 210. A prescribed cumulative dose of radiation therapy may thereby be delivered to the therapy locus while damage to tissue near the therapy locus may be reduced or avoided.

In some examples, surface camera imaging data may be acquired using one or more surface cameras 138A-138C. FIG. 2A depicts one non-limiting example in which one or more surface cameras 138A, 138B may be affixed to a ceiling 215 in the therapy treatment room and/or one or more surface cameras 138C may be affixed to a wall 217 in the therapy treatment room. One or more of the surface cameras 138A-138C may acquire surface camera imaging data in real time. The surface camera imaging data from one or more of the surface cameras 138A-138C may then be transmitted to an image processing device, such as to the image processing device 112 of FIG. 1, to generate a model.

Figure 2B:
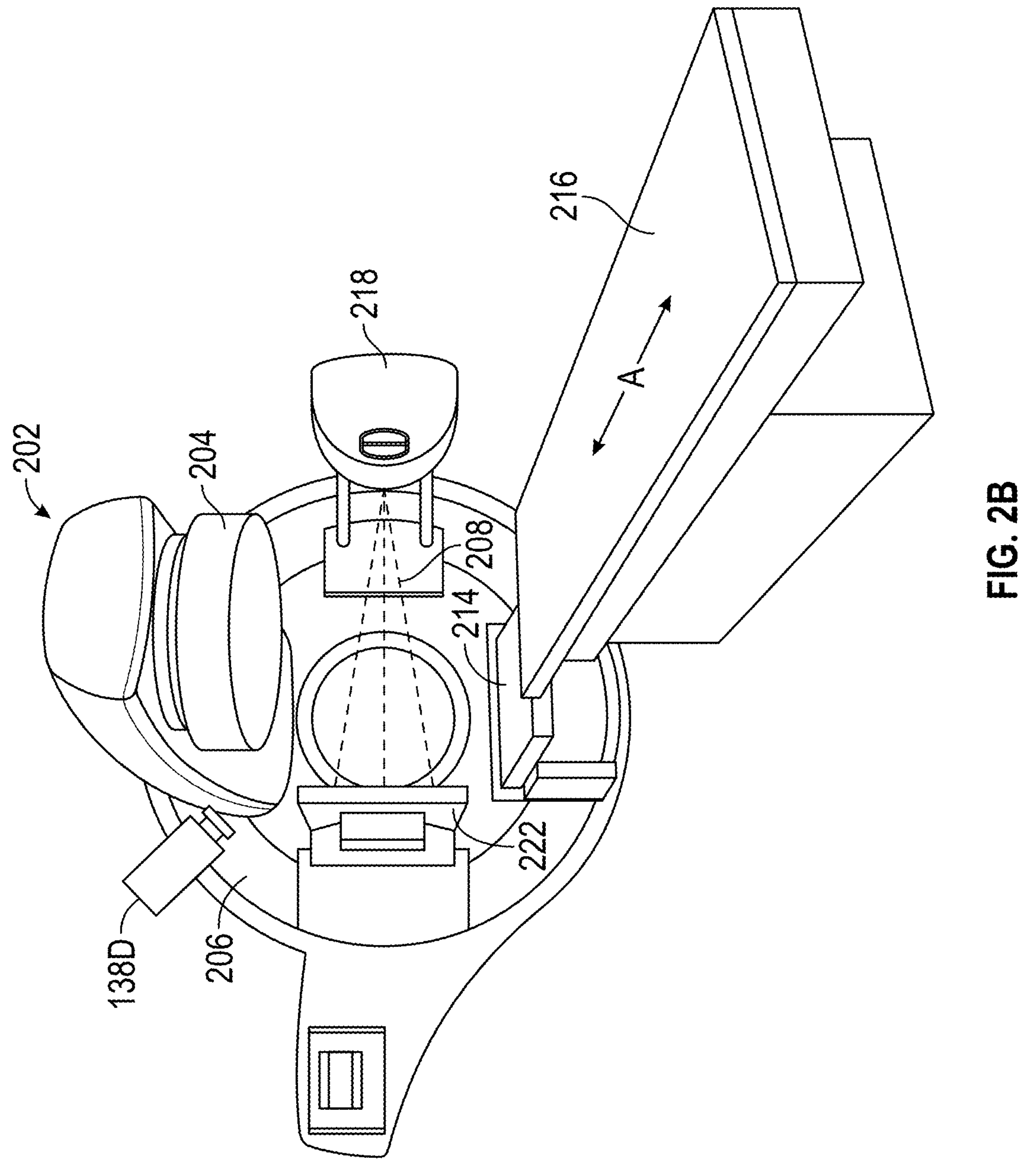
FIG. 2B illustrates an example of a system including a combined radiation therapy system and an imaging system, such as a cone beam computed tomography (CBCT) imaging system, according to some embodiments of the present disclosure.

FIG. 2B illustrates an example of a radiation therapy device 202 that may include a combined linac and an imaging system, such as may include a CT imaging system. The radiation therapy device 202 may include an MLC (not shown). The CT imaging system may include an imaging X-ray source 218, such as providing X-ray energy in a kiloelectron-Volt (keV) energy range which may be used for imaging the patient's anatomy, such as portal imaging (e.g., to provide real X-ray measurements). The imaging X-ray source 218 (also referred to as a "kV source" for kV imaging) may provide a fan-shaped and/or a conical beam 208 directed to an imaging detector 222, such as a flat panel detector. The radiation therapy device 202 may be similar to the system described in relation to FIG. 2A, such as including a radiation therapy output 204, a gantry 206, a couch 216, and another imaging detector 214 (such as a flat panel detector). The X-ray source 218 may provide a comparatively-lower-energy X-ray diagnostic beam, for imaging.

In the illustrative embodiment of FIG. 2B, the radiation therapy output 204, e.g., MV source, and the X-ray source 218, e.g., kV source, may be mounted on the same rotating gantry 206, rotationally-separated from each other by 90 degrees. This arrangement may enable imaging perpendicular to the beam of radiation output by radiation therapy output 204, which, in some embodiments, may be a Megavolt (MV) treatment beam. The kV source 218 may be used to acquire 2D X-ray projections for kV imaging as the kV source 218 moves around the patient along gantry 206.

In another embodiment, two or more X-ray sources may be mounted along the circumference of the gantry 206, such as each having its own detector arrangement to provide multiple angles of diagnostic imaging concurrently.

Similarly, multiple radiation therapy outputs 204 may be provided.

FIG. 2B depicts another non-limiting example in which one or more surface cameras 138D may acquire surface camera imaging data. In the example shown in FIG. 2B, a surface camera 138D may be affixed to a frontside of a radiation therapy device 202, such as to a frontside of a CT bore and another surface camera may be affixed to a backside of the radiation therapy device 202, such as to a backside of a CT bore. In this manner, the surface cameras may provide a continuous view of the patient. The surface camera imaging data from the surface cameras, such as the surface camera 138D and a backside surface camera may then be transmitted to an image processing device, such as to the image processing device 112 of FIG. 1, to generate a model.

Figure 3:
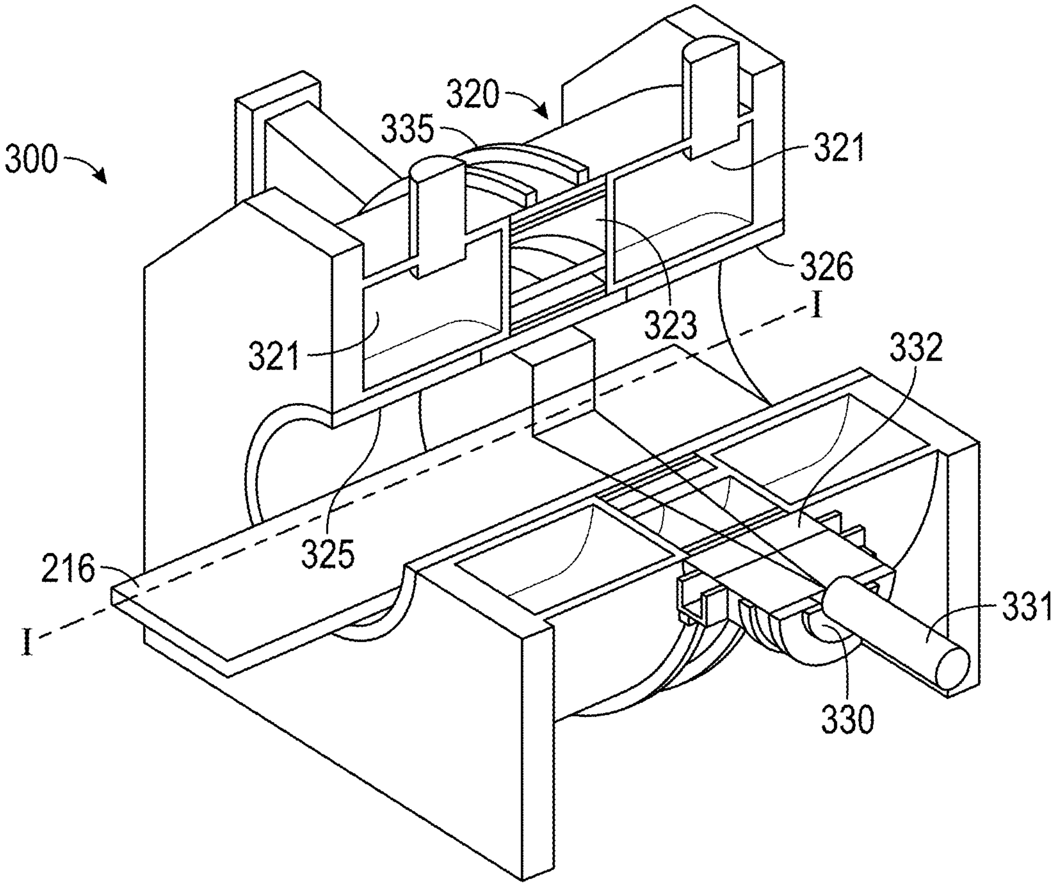
FIG. 3 illustrates a partially cut-away view of an example system including a combined radiation therapy system and an imaging system, such as a nuclear MR imaging (MM) system, according to some embodiments of the present disclosure.
Figure 4B:
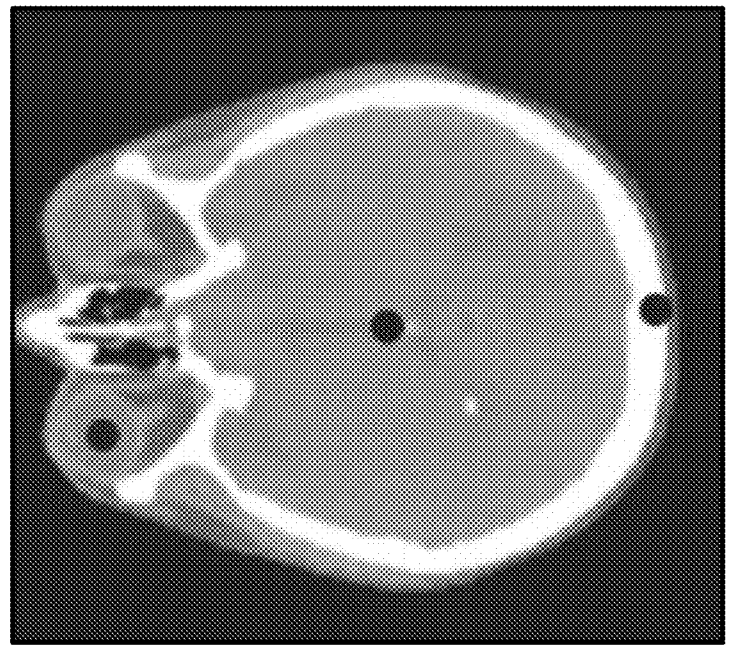
FIGS. 4A and 4B depict the differences between an example MRI image and a corresponding CT image, respectively, according to some embodiments of the present disclosure.
Figure 4A:
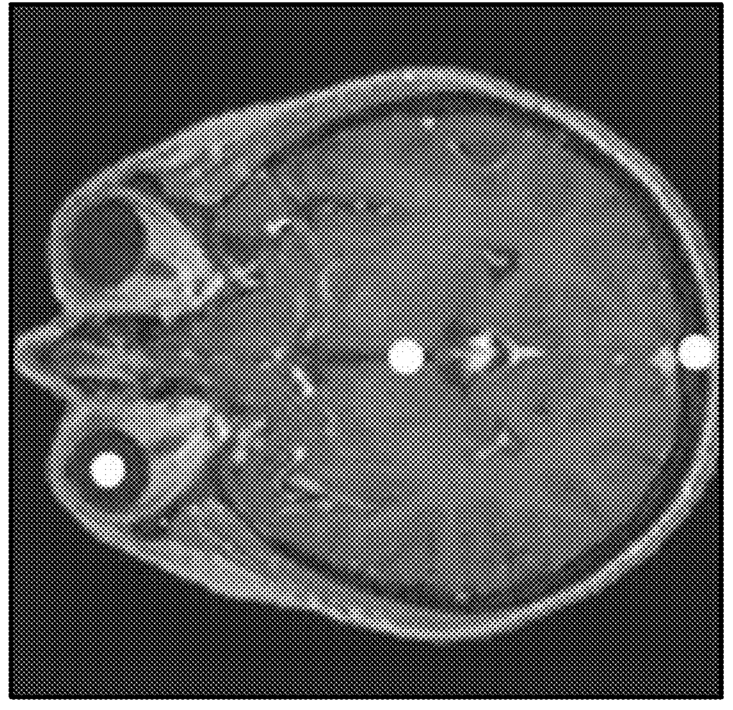

FIG. 3 depicts an example radiation therapy system 300 that may include combining a radiation therapy device 202 and an imaging system, such as a nuclear MR imaging system (e.g., known in the art as an MR-linac) consistent with the disclosed embodiments. As shown, system 300 may include a couch 216, an image acquisition device 320, and a radiation delivery device 330. System 300 delivers radiation therapy to a patient in accordance with a radiotherapy treatment plan. In some embodiments, image acquisition device 320 may correspond to image acquisition device 132 in FIG. 1 that may acquire origin images of a first modality (e.g., MRI image shown in FIG. 4A) or destination images of a second modality (e.g., CT image shown in FIG. 4B).

Couch 216 may support a patient (not shown) during a treatment session. In some implementations, couch 216 may move along a horizontal translation axis (labelled "I"), such that couch 216 may move the patient resting on couch 216 into and/or out of system 300. Couch 216 may also rotate around a central vertical axis of rotation, transverse to the translation axis. To allow such movement or rotation, couch 216 may have motors (not shown) enabling the couch 216 to move in various directions and to rotate along various axes. A controller (not shown) may control these movements or rotations in order to properly position the patient according to a treatment plan.

In some embodiments, image acquisition device 320 may include an MRI machine used to acquire 2D or 3D MRI images of the patient before, during, and/or after a treatment session. Image acquisition device 320 may include a magnet 321 for generating a primary magnetic field for magnetic resonance imaging. The magnetic field lines generated by operation of magnet 321 may run substantially parallel to the central translation axis I. Magnet 321 may include one or more coils with an axis that runs parallel to the translation axis I. In some embodiments, the one or more coils in magnet 321 may be spaced such that a central window 323 of magnet 321 is free of coils. In other embodiments, the coils in magnet 321 may be thin enough or of a reduced density such that they are substantially transparent to radiation of the wavelength generated by radiotherapy device 330. Image acquisition device 320 may also include one or more shielding coils, which may generate a magnetic field outside magnet 321 of approximately equal magnitude and opposite polarity in order to cancel or reduce any magnetic field outside of magnet 321. As described below, radiation source 331 of radiotherapy device 330 may be positioned in the region where the magnetic field is cancelled, at least to a first order, or reduced.

Image acquisition device 320 may also include three sets of gradient coils, which may generate magnetic field gradients that are superimposed on the primary magnetic field. Each set of gradient coils may generate a gradient along a corresponding one of the x-axis, y-axis, and z-axis. Each gradient coil may include two sections, shown at reference numbers 325 and 326. All three sets of gradient coils may be physically located at reference numbers 325 and 326.

The gradient coils may generate a gradient in the resultant magnetic field that allows spatial encoding of the protons so that their position may be determined. The gradient coils may be positioned around a common central axis with the magnet 321.

In some embodiments, image acquisition device 320 may be an imaging device other than an MRI, such as an X-ray, a CT, a CBCT, a spiral CT, a PET, a SPECT, an optical tomography, a fluorescence imaging, ultrasound imaging, radiotherapy portal imaging device, or the like. As would be recognized by one of ordinary skill in the art, the above description of image acquisition device 320 concerns certain embodiments and is not intended to be limiting.

Radiotherapy device 330 may include the radiation source 331, such as an X-ray source or a linac, and an MLC 332 (shown below in FIG. 5). Radiotherapy device 330 may be mounted on a chassis 335. One or more chassis motors (not shown) may rotate chassis 335 around couch 216 when couch 216 is inserted into the treatment area. In an embodiment, chassis 335 may be continuously rotatable around couch 216 when couch 216 is inserted into the treatment area. Chassis 335 may also have an attached radiation detector (not shown), preferably located opposite to radiation source 331 and with the rotational axis of chassis 335 positioned between radiation source 331 and the detector. Further, device 330 may include control circuitry (not shown) used to control, for example, one or more of couch 216, image acquisition device 320, and radiotherapy device 330. The control circuitry of radiotherapy device 330 may be integrated within system 300 or remote from it.

During a radiotherapy treatment session, a patient may be positioned on couch 216. System 300 may then move couch 216 into the treatment area defined by magnet 321, coils 325 and 326, and chassis 335. Control circuitry may then control radiation source 331, MLC 332, and the chassis motor(s) to deliver radiation to the patient through the window between coils 325 and 326 according to a radiotherapy treatment plan.

FIG. 2A, FIG. 2B, and FIG. 3 illustrate generally embodiments of a radiation therapy device configured to provide radiotherapy treatment to a patient, including a configuration where a radiation therapy output may be rotated around a central axis (e.g., an axis "A"). Other radiation therapy output configurations may be used. For example, a radiation therapy output may be mounted to a robotic arm or manipulator having multiple degrees of freedom. In yet another embodiment, the therapy output may be fixed, such as located in a region laterally separated from the patient, and a platform supporting the patient may be used to align a radiation therapy isocenter with a specified target locus within the patient.

As discussed above, radiation therapy devices described by FIG. 2A, FIG. 2B, and FIG. 3 include an MLC for shaping, directing, or modulating an intensity of a radiation therapy beam to the specified target locus within the patient.

Figure 5:
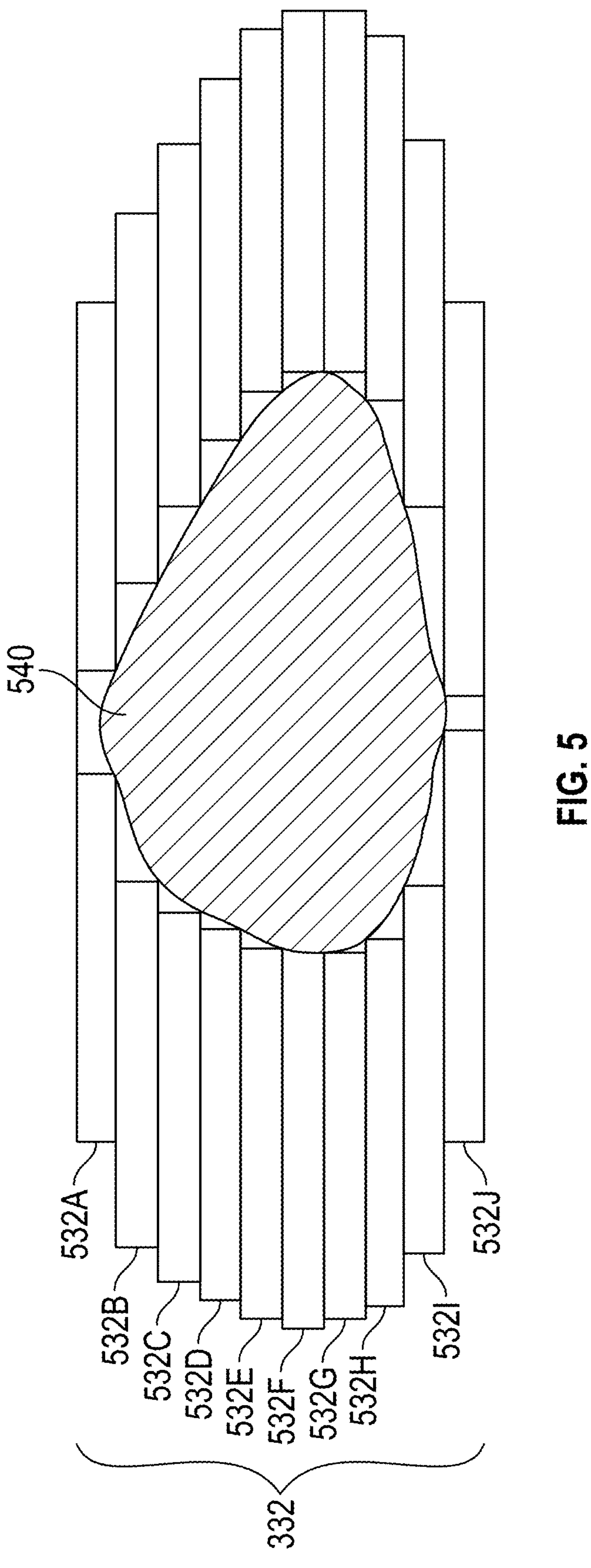
FIG. 5 illustrates an example of a collimator configuration for shaping, directing, or modulating an intensity of a radiation therapy beam, according to some embodiments of the present disclosure.

FIG. 5 illustrates an example of an MLC 332 that includes leaves 532A through 532J that may be automatically positioned to define an aperture approximating a tumor 540 cross section or projection. The leaves 532A through 532J permit modulation of the radiation therapy beam. The leaves 532A through 532J may be made of a material specified to attenuate or block the radiation beam in regions other than the aperture, in accordance with the radiation treatment plan. For example, the leaves 532A through 532J may include metallic plates, such as comprising tungsten, with a long axis of the plates oriented parallel to a beam direction and having ends oriented orthogonally to the beam direction (as shown in the plane of the illustration of FIG. 2A). A "state" of the MLC 332 may be adjusted adaptively during a course of radiation therapy treatment, such as to establish a therapy beam that better approximates a shape or location of the tumor 540 or another target locus. This is in comparison to using a static collimator configuration or as compared to using an MLC 332 configuration determined exclusively using an "offline" therapy planning technique. A radiation therapy technique using the MLC 332 to produce a specified radiation dose distribution to a tumor or to specific areas within a tumor may be referred to as IMRT.

Figure 6:
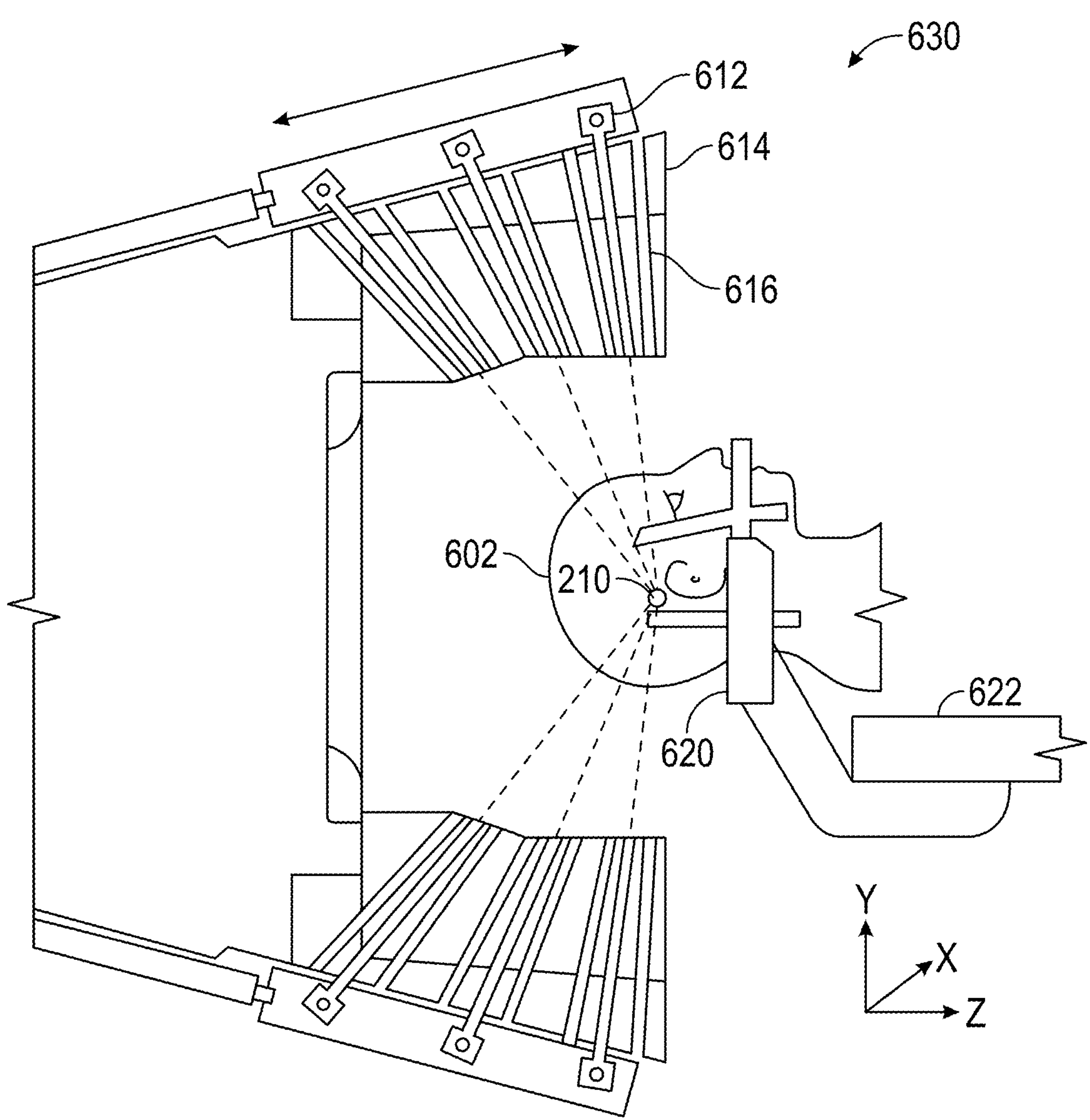
FIG. 6 illustrates an example of a Gamma Knife® radiation therapy system, according to some embodiments of the present disclosure.

FIG. 6 illustrates an embodiment of another type of radiotherapy device 630 (e.g., a Leksell Gamma Knife®), according to some embodiments of the present disclosure. As shown in FIG. 6, in a radiotherapy treatment session, a patient 602 may wear a coordinate frame 620 to keep stable the patient's body part (e.g., the head) undergoing surgery or radiotherapy. Coordinate frame 620 and a patient positioning system 622 may establish a spatial coordinate system, which may be used while imaging a patient or during radiation surgery. Radiotherapy device 630 may include a protective housing 614 to enclose a plurality of radiation sources 612. Radiation sources 612 may generate a plurality of radiation beams (e.g., beamlets) through beam channels 616. The plurality of radiation beams may be configured to focus on an isocenter 210 from different directions. While each individual radiation beam may have a relatively low intensity, isocenter 210 may receive a relatively high level of radiation when multiple doses from different radiation beams accumulate at isocenter 210. In certain embodiments, isocenter 210 may correspond to a target under surgery or treatment, such as a tumor.

In radiation treatment planning, using a computer system configured with software for allowing a physician or other user to perform manual structure contouring (e.g., of a region of interest (ROI) or organ-at-risk (OAR)) and manual contour editing, such user-driven contouring, may be a time-consuming process. Instead, an automated tool (e.g., ABAS provided by Elekta AB, Sweden) can be used to assist in identifying or delineating the target tumor and organs at risk. A radiation therapy treatment plan ("treatment plan") can then be created using an optimization technique based on clinical and dosimetric objectives and constraints (e.g., the maximum, minimum, and fraction of dose of radiation to a fraction of the tumor volume ("95% of target shall receive no less than 100% of prescribed dose"), and like measures for the critical organs). The optimized plan is comprised of numerical parameters that specify the direction, cross-sectional shape, and intensity of each radiation beam.

Automatic contouring based on machine learning has become increasingly common, due to their capacity to produce highly accurate and reliable contours in a fraction of the time required by a manual rater. However, such models require vast training sets (consisting of many pairs of images and training labels) from which to learn. As such, the development of accurate machine learning models bears a considerable cost associated with the collection and curation of large sets of training data.

This disclosure describes using joint training techniques to train multiple models across clinical datasets for automatic contouring. As described below, rather than using separate deep neural networks that are trained independently for each different dataset corresponding to different combinations of image parameters (e.g., a different image contrast or anatomy), joint training can be used to train multiple models simultaneously across clinical datasets for automatic contouring. By taking advantage of commonalities between two or more datasets, the techniques of this disclosure effectively take advantage of data that would otherwise be considered irrelevant to the task—allowing the user to train more performant models while requiring less training data per dataset.

Figures 7, 8:
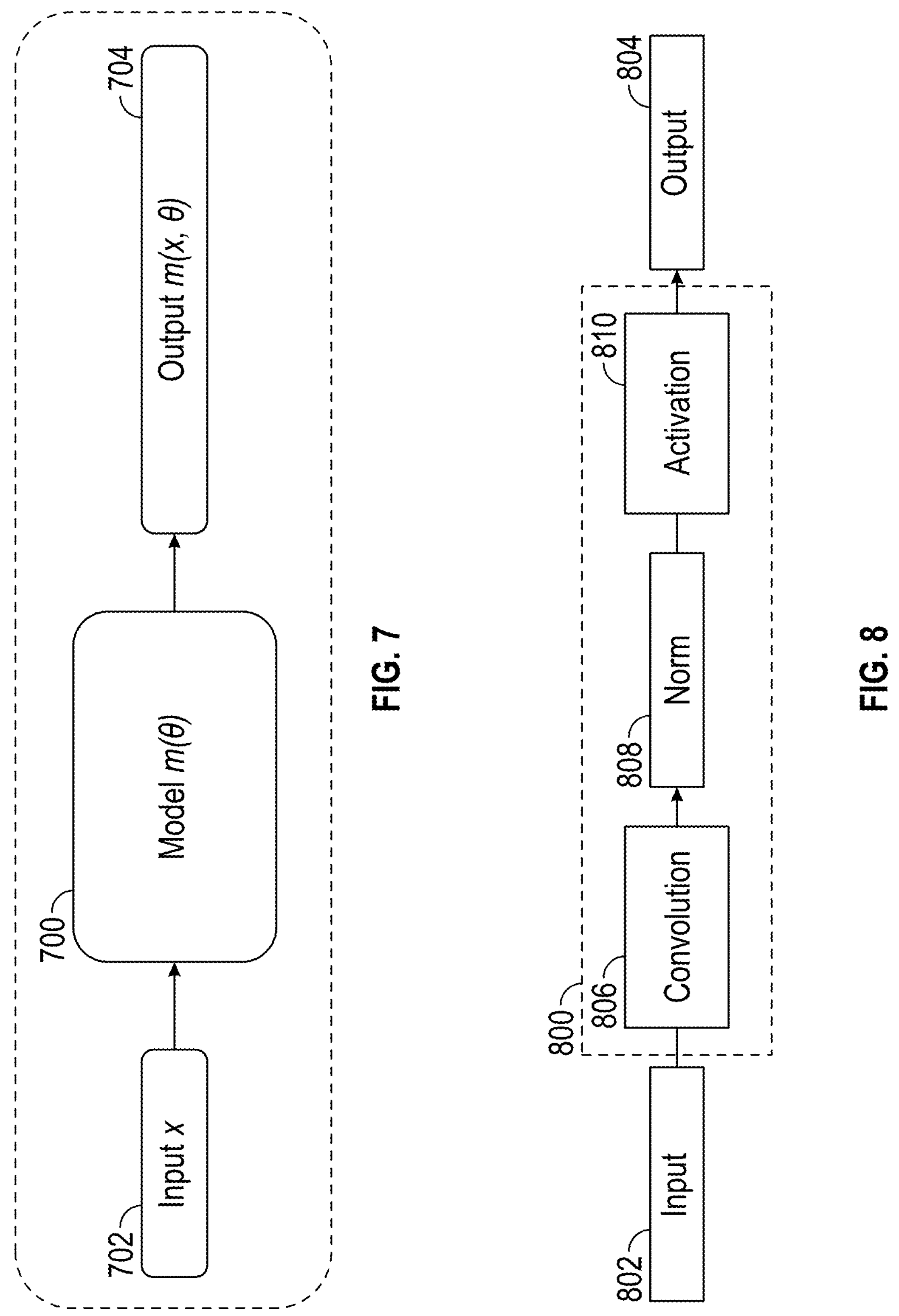
FIG. 7 is a conceptual diagram of a classical machine learning model.
FIG. 8 is a conceptual diagram depicting a convolutional block of the classical machine learning model of FIG. 7.

FIG. 7 is a conceptual diagram of a classical machine learning model 700. In the classical method, different models representing different combination of image parameters (e.g., prostate T1-weighted model versus prostate T2-weighted model, versus female pelvis T2-weighted model) are trained independently, each using a large dedicated input training dataset. The machine learning model 700 receives input 702 and generates an output 704.

Let $\{x_i, y_i\}$ be the ith training sample in a training dataset, each sample consisting of a training image and ground-truth segmentation respectively. In the classical setting, a model for this dataset is trained by iteratively optimizing the network parameters towards a minimal loss using Equation 1 below:

$$\theta = \operatorname{argmin} \sum_i L(m(x_i, \theta), y_i) \qquad \text{Equation 1}$$

where m is the model and θ are the respective model parameters. Common choices for the loss function L includes the cross-entropy, soft Dice loss, or a weighted combination thereof. Iterative optimization is carried out via stochastic gradient descent (or an adaptive variant) on mini-batches of training samples, until some predefined convergence criteria is met.

FIG. 8 is a conceptual diagram depicting a convolutional block of the classical machine learning model of FIG. 7. The convolutional block 800 (of the machine learning model 700 of FIG. 7) receives input 802 and generates an output 804. The convolutional block 800 includes a convolution layer 806 (with learnable weights), a normalization layer 808, and a final activation layer 810. As an example, convolutional neural networks (CNNs) are built by stacking convolutional blocks.

Figures 9, 10:
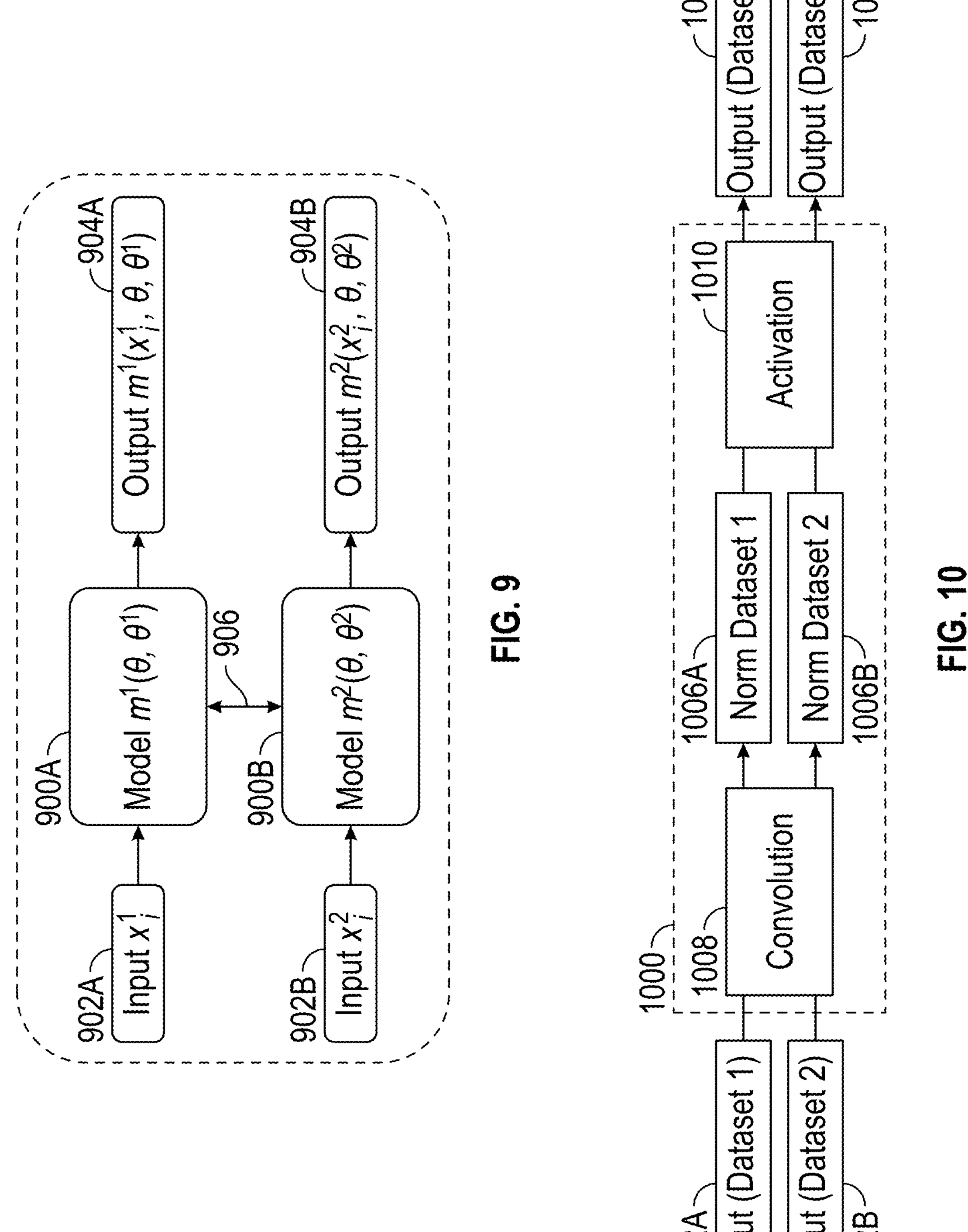
FIG. 9 is conceptual diagram of a joint machine learning model using the techniques of this disclosure.
FIG. 10 is a conceptual diagram depicting a convolutional block of a convolutional neural network of a jointly trained machine learning model using the techniques of this disclosure.

In contrast to the classical model, the techniques of this disclosure jointly train two or more models using two or more datasets (see FIG. 9).

FIG. 9 is conceptual diagram of a joint machine learning model using the techniques of this disclosure. In the joint model, two or more coupled models (containing shared parameters) are jointly trained on two or more respective input datasets, allowing the user to train more performant models while requiring less training data per dataset.

A first machine learning model 900A receives input 902A and generates an output 904A. A second machine learning model 900B receives input 902B and generates an output 904B, where the input 902B is separate from input 902A and the output 904B is separate from the output 904A. The machine learning model 900A, 900B are jointly trained because they share parameters θ.

Each model 900A, 900B can generate outputs having different anatomical structures. For example, the first model 900A can generate a first output 904A having a first set of anatomical structures and the second model 900B can generate a second output 904B having a second set of anatomical structures that is different from the first set of anatomical structures. For example, if the two models 900A, 900B were jointly trained using male and female pelvises, the first model 900A can generate an output 904A having male anatomical structures and the second model 900B can generate an output 904B having female anatomical structures.

Let $$\{x_i^n, y_i^n\}$$

be the ith training sample for dataset n, with each training sample consisting of a training image and ground-truth segmentation, respectively. Let each model now be parameterized by two sets of parameters: a set of model-specific parameters $\theta^n$ and a set of shared parameters θ. In the joint training setting, all parameters are simultaneously optimized using Equation 2 as follows:

$$\{\theta^n\}_{n=1,\ldots,N}, \theta = \operatorname{argmin} \sum_n w^n \sum_i L(m^n(x_i^n, \theta^n, \theta), y_i^n) \qquad \text{Equation 2}$$

where the total loss to be minimized is now a composite function containing one term from each dataset, each optionally weighted by a positive scalar $w^n$. As in the classical setting, optimization of the parameters in the joint training setting is done via stochastic gradient descent on mini-batches of training samples. In practice, each batch may consist of one or more samples from each dataset, or training batches may be alternatively sampled from the various datasets.

In this manner, the machine learning model 900A, 900B may be trained simultaneously, such as by sharing at least one parameter θ during the training. Jointly training the machine learning models 900A, 900B may include inputting a first training dataset of a first type to train a first one of the machine learning models, e.g., input 902A applied to the machine learning model 900A in FIG. 9, where the first machine learning model 900A is configured to use at least one first parameter $\theta^1$ and a shared parameter θ. Jointly training the machine learning models 900A, 900B may include inputting a second training dataset of a second type to a second one of the machine learning models, e.g., input 902B applied to the machine learning model 900B in FIG. 9, where the first type is different than the second type, where the second machine learning model 900B is configured to use at least one second parameter $\theta^2$ and the shared parameter θ, and where the second machine learning model 900B is coupled, such as via a connection or coupling 906, to the first machine learning model 900A to share the parameter θ.

As a non-limiting example, the machine learning models 900A, 900B may use a convolutional neural network. Convolutional neural networks (CNN) have various parameters that are the filters that the model learns. The parameters of both of the machine learning models 900A, 900B may be updated at the same time using all of the available pooled training data. During an optimization process in which the loss function described above is minimized, convolution filters are updated. Because the machine learning models 900A, 900B are jointly trained, they are also optimized at the same time, which means that the shared parameters θ and the model-specific parameters $\theta^1$ and $\theta^2$ are optimized simultaneously (images from input dataset 1 will cause an update of parameters θ and $\theta^1$, images from input dataset 2 will cause an update of parameters θ and $\theta^2$).

In some examples, the first type includes a T1-weighted image and the second type includes a T2-weighted image. In some examples, the first type includes either a T1-weighted image or a T2-weighted image having a short scan time, e.g., a 2-minute T2-weighted MRI image, and the second type includes either a T1-weighted image or a T2-weighted image having a longer scan time, e.g., a 6-minute T2-weighted MM image.

In some examples, the first type includes an anatomy of a male subject and the second type includes an anatomy of a female subject. In some examples, the first type includes a male pelvic region and the second type includes female pelvic region.

In some examples, the first type includes a female subject having had a hysterectomy and the second type includes a female subject not having had a hysterectomy. In some examples, the first type includes a male subject having had a prostate removed and the second type includes a male subject not having had a prostate removed.

The machine learning models 900A, 900B may be jointly trained simultaneously using the first and second types of training datasets such that features common to both datasets can be shared between the models. As an example, one can jointly train male and female pelvis models, effectively doubling the number of training examples for any OAR that is common to both training datasets (e.g., bony anatomy, bladder, and rectum).

For example, male and female pelvises have some common features, such as bladder contour, femur contour, and pelvis contour and anatomy-specific features, such as prostate contour, seminal vesicle contour, penile bulb contour for the male pelvis and uterocervic contour, vagina contour for the female pelvis As such, various parameters θ may be shared between the machine learning models 900A, 900B. Other parameters $\theta^n$ may be specific to the particular machine learning models 900A, 900B and, as such, are not shared between the models. By taking advantage of commonalities between these two (or more) datasets, the techniques of this disclosure effectively take advantage of data that would otherwise be considered irrelevant to the task—allowing the user to train more performant models while requiring less training data per dataset.

This approach can also be used to jointly training various (similar) models to better cope with differences in anatomy due to pre-treatment ablative surgeries (e.g., prostatectomy, hysterectomy, etc.)

When trained, the machine learning model 900A, 900B are configured to automatically contour images for radiotherapy treatment. A system, such as the radiotherapy system 100 of FIG. 1, may generate a radiotherapy treatment plan for a subject, to automatically contour an image depicting an anatomy of the subject using processing circuitry, such as in FIG. 1 or FIG. 14, that is configured to implement at least one of the jointly trained machine learning model.

FIG. 10 is a conceptual diagram depicting a convolutional block of a convolutional neural network of a jointly trained machine learning model using the techniques of this disclosure. The first machine learning model 900A of FIG. 9 and the second machine learning model 900B of FIG. 9 both share the same convolutional blocks. Within each convolutional block some layers are shared among models 900A and 900B and some layers are specific to each model. In this example, the convolutional layers 1002 and the activation layers 1006 are common to both models. As such, learnable parameters of the convolutional layers and activation layers are part of the shared parameters θ. However, different normalization layers 1004A and 1004B are used respectively for model 900A and 900B. As such, parameters that belong to the normalization layers are part of the model-specific parameters ($\theta^1$ and $\theta^2$). As an example, convolutional neural networks (CNNs) 900A and 900B are both built by stacking the same convolutional blocks 1000.

The convolutional neural networks (CNNs) 900A and 900B, which include the same stack of convolutional blocks 1000), receive as input samples drawn from any dataset (input 1002A or input 1002B) and generate corresponding outputs (output 1004A or output 1004B). When the input comes from dataset 1002A, then the normalization layers 1006A are used. When the input comes from dataset 1002B, then the normalization layers 1006B are used instead. The inputs 1002A, 1002B may include training datasets to train the machine learning models. Or, if the machine learning models have already been trained, an input 1002A (or input 1002B) may include image data specific to a subject scheduled to receive radiotherapy treatment.

In comparison to the convolutional block 800 of FIG. 8, the convolutional block 1000 also include a convolution layer 1008 (with optional learnable weights). The normalization layer of FIG. 8, however, is replaced by two (or more) layers: a first normalization layer 1006A and a second normalization layer 1006B. Inside the convolutional block 1000, the output of the convolution layer 1008 is normalized using dataset-specific parameters depending on the source of the input (e.g., whether the input of the convolutional block 1000 comes from dataset 1002A or dataset 1002B). In other words, shared parameters θ does not include parameters from normalization layers. In FIG. 10, the first normalization layer 1006A is associated with the first training dataset (first input 1002A) and the second normalization layer 1006B is associated with the second training dataset (second input 1002B).

Regardless of the source of the input, the data is processed using the same (shared) convolutional layer. As such, all the convolutional weights that make up the convolutional filters of the CNN are all the same across the datasets. But, as mentioned above, dataset-specific normalization layers are used to account for a small set of model-specific parameters. When a sample passes through the CNN, the sample chooses the appropriate normalization layer specific to the dataset with which the sample is associated. All the other parameters are shared with the other models.

A set of jointly trainable models can be obtained by replacing the standard convolutional blocks 800 of FIG. 8 with those described here. Although two machine learning models 900A, 900B are described in this document for purpose of simplicity, there may be N machine learning models, with the normalization layer of FIG. 8 replaced with N normalization layers.

Normalization layers (e.g., batch, group, instance, and layer normalization layers) are widely used components in modern deep neural networks. For example, batch normalization re-calibrates intermediate features maps f produced in the network in a per-channel fashion according to Equation 3:

$$\hat{f}_c = \alpha_c\left(\frac{f_c - E(f_c)}{\mathrm{Var}(f_c) + \epsilon}\right) + \beta_c \quad \text{Equation 3}$$

where c is the channel index, the expectation E, and variance Var terms are statistics estimated by running-averages of $f_c$, $\epsilon$ is a small constant to ensure numerical stability, and the $\alpha$ and $\beta$ terms are learnable parameters.

The convolutional block 1000 further includes a final activation layer 1010, which operates on the output of both normalization layers 1006A and 1006B with the same shared parameters. The outputs 1004A, 1004B are associated with corresponding inputs 1002A, 1002B. For example, if the models were jointly trained using an input 1002A having T1-weighted images and an input 1002B having T2-weighted images, then the output 1004A includes automatically contoured structures of T1-weighted images and the output 1004B includes automatically contoured structures of T2-weighted images. As such, models trained on different MR contrast (e.g., T1-weighted versus T2-weighted) can contour a different set of structures (e.g., structures that are only available on T1-weighted or T2-weighted images and structures that are available on both images). When using a previously trained machine learning model, such as the model 900A of FIG. 9, which was trained using T1-weighted images, a T1-weighted image of a first subject scheduled to receive radiotherapy treatment may be applied as input 1002A to generate output 1004A and a T2-weighted image of a second subject scheduled to receive radiotherapy treatment may be applied as input 1002B to generate output 1004B.

Beginning with a chosen backbone segmentation network (e.g. U-Net, ResU-Net, etc.), a set of shared models can be constructed as follows:

Each internal normalization layer is replaced by a set of N normalization layers, where Nis the number of datasets; and The output layer of the segmentation network (not shown) is replaced by a set of N such layers, each with the appropriate number of output channels (e.g. corresponding to the number of structures for the respective dataset). This allows two jointly trained networks to produce different set of output structures.

Then, for an input from dataset n, internal normalization is performed, at each applicable network layer, by the nth normalizer in the set. Likewise, the nth output layer is selected and applied. Thus, each model shares all network parameters except for the set of normalization parameters (e.g., {$\alpha$, $\beta$}) and the parameters associated with the final output layer. This strategy may be performed using any choice of parameterized internal normalization scheme (e.g. batch, group or instance normalization). Alternate embodiments may also be considered (e.g., each dataset model is a U-Net where the encoder/decoder/bottleneck layer is shared across models).

Figures 11, 12:
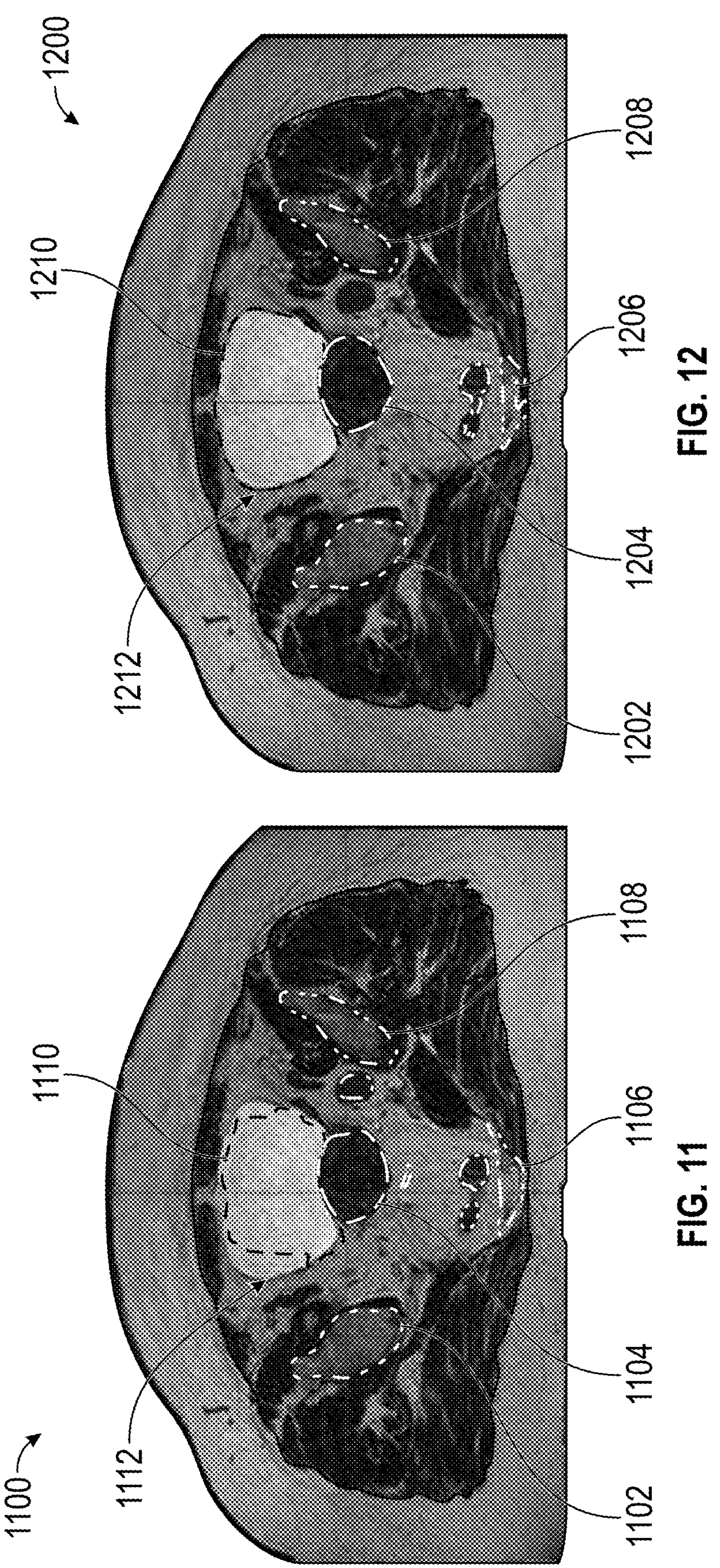
FIG. 11 is an MRI image of a female pelvis automatically contoured using a small set of female pelvis training data.
FIG. 12 is an MRI image of the female pelvis of FIG. 11 automatically contoured using a model jointly trained using the techniques of this disclosure using the small set of female pelvis training data of FIG. 11 and an additional larger set of male pelvis training data.

FIG. 11 is an MRI image 1100 of a female pelvis automatically contoured using a small set of female pelvis training data. In the image 1100, several contours of anatomy are depicted, including contours 1102-1110. The bladder contour 1110 is shown adjacent the bladder 1112.

FIG. 12 is an MRI image 1200 of the female pelvis of FIG. 11 automatically contoured using a model jointly trained using the techniques of this disclosure using the small set of female pelvis training data of FIG. 11 and an additional larger set of male pelvis training data. In the image 1200, several contours of anatomy are depicted, including contours 1202-1210. The bladder contour 1210 is shown adjacent the bladder 1212. As seen graphically, the jointly trained machine learning model produces a more accurate bladder contour 1210 than the bladder contour 1110 of FIG. 11.

Rather than take the individual sets of data and then use them to train one model per clinical dataset, as is conventionally done, the techniques of this disclosure leverage the commonalities between different datasets to allow us to train models effectively using less data (in the example of FIG. 12, joint training is used to train a female model with better quality using the same amount of female pelvis training data used in the example of FIG. 11). Using the techniques of this disclosure, a machine learning model may be better trained using less training data due to the commonalities associated with the different training datasets.

Figure 13:
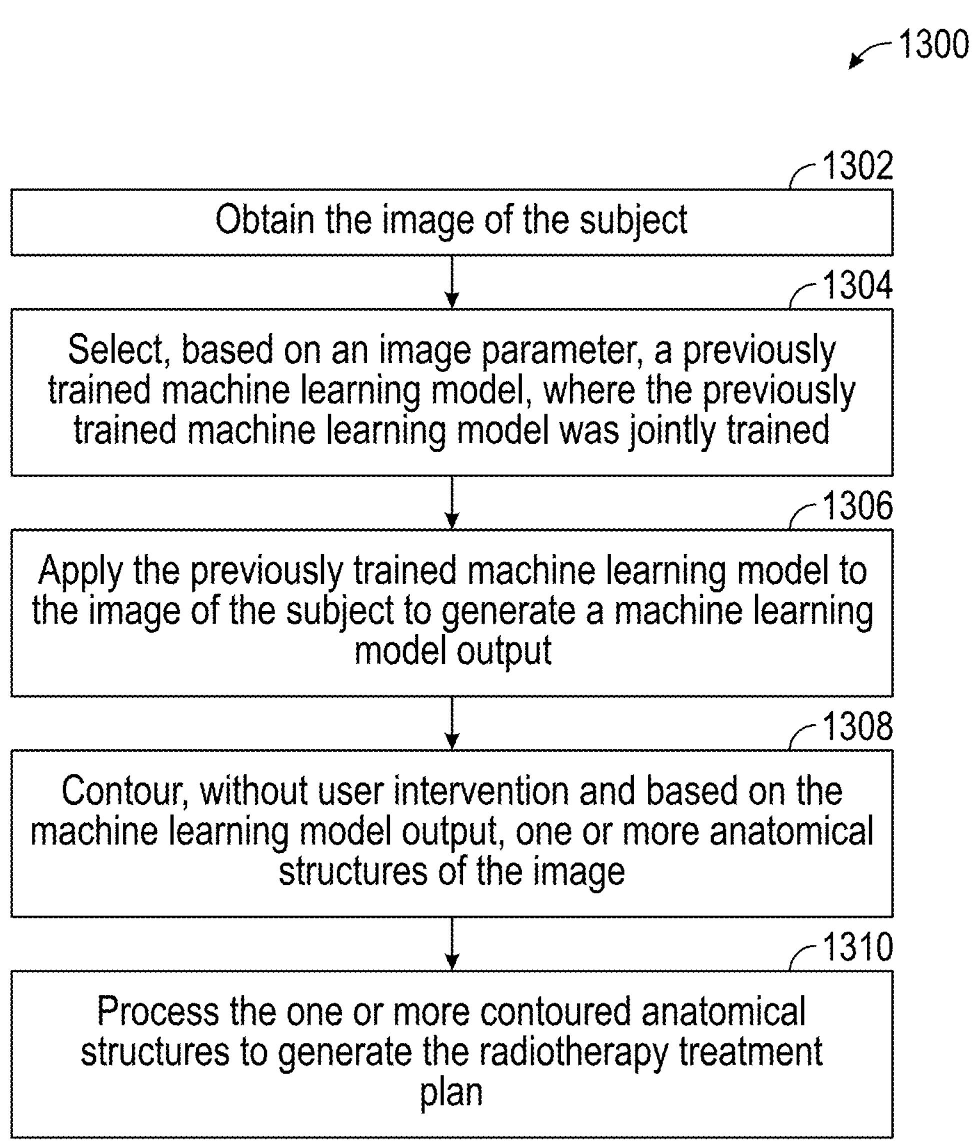
FIG. 13 is a flow diagram of an example of a computer-implemented method for generating a radiotherapy treatment plan for a subject including automatically contouring an image depicting an anatomy of the subject.

FIG. 13 is a flow diagram of an example of a computer-implemented method 1300 for generating a radiotherapy treatment plan for a subject including automatically contouring an image depicting an anatomy of the subject. At block 1302, the method 1300 includes obtaining the image of the subject.

At block 1304, the method 1300 includes selecting, based on an image parameter, a previously trained machine learning model, where the previously trained machine learning model was jointly trained, e.g., where parameters are shared simultaneously between the previously trained machine learning model and another previously trained machine learning model. Image parameters may include, for example, whether the subject had male or female anatomy, whether the image was a T1-weighted image or T2-weighted image, and/or whether the image had a short (lower resolution) or long (higher resolution) scan time.

At block 1306, the method 1300 includes applying the previously trained machine learning model to the image of the subject to generate a machine learning model output.

At block 1308, the method 1300 includes automatically contouring, e.g., without user intervention and based on the machine learning model output, one or more anatomical structures of the image.

At block 1310, the method 1300 includes processing the one or more contoured anatomical structures to generate the radiotherapy treatment plan.

After generating the radiotherapy treatment plan, a system, such as the radiotherapy system 100 of FIG. 1, may deliver the radiotherapy treatment to the subject.

In some examples, the previously trained machine learning model was trained using anatomies of female subjects having had hysterectomies and female subjects not having had hysterectomies (in this example, the only difference between the two models is that one model will output an additional uterocervix structure). A similar example is a machine learning model previously trained using anatomies of male pelvis having had prostatectomy and male pelvis not having had prostatectomy (in this example, the only difference between the two models is that one model will output an additional prostate structure).

In some examples, the previously trained machine learning model was trained using T1-weighted images and T2-weighted images. In some examples, the previously trained machine learning model was trained using T2-weighted images and T2-weighted images with different scan times and a different set of output structures.

In some examples, the previously trained machine learning model was trained using anatomies of male subjects and female subjects. In some such examples, the anatomies of the male subjects and the female subjects include anatomies of male pelvic regions and female pelvic regions.

Figure 14:
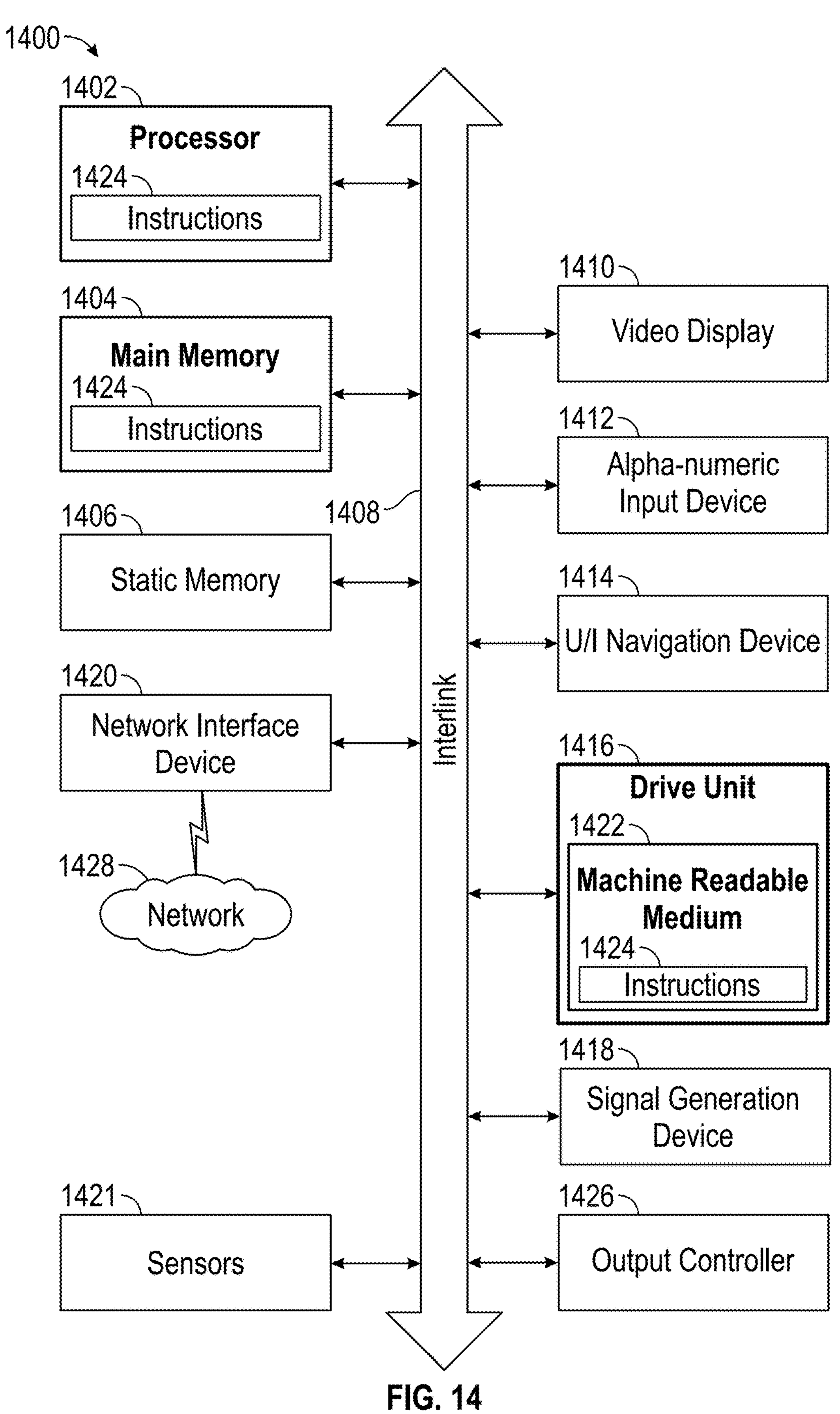
FIG. 14 illustrates a block diagram of an embodiment of a machine on which one or more of the methods as discussed herein may be implemented.

FIG. 14 illustrates a block diagram of an embodiment of a machine 1400 on which one or more of the methods as discussed herein may be implemented. In one or more embodiments, one or more items of the image processing device 112 may be implemented by the machine 1400. In alternative embodiments, the machine 1400 operates as a standalone device or may be connected (e.g., networked) to other machines. In one or more embodiments, the image processing device 112 may include one or more of the items of the machine 1400. In a networked deployment, the machine 1400 may operate in the capacity of a server or a client machine in server-client network environment, or as a peer machine in a peer-to-peer (or distributed) network environment. The machine 1400 may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine 1400 is illustrated, the term "machine" shall also be taken to include any collection of machines that individually or jointly execute a set (or multiple sets) of instructions to perform any one or more of the methodologies discussed herein.

The example machine 1400 includes processing circuitry (e.g., the processor 1402, a CPU, a GPU, an ASIC, circuitry, such as one or more transistors, resistors, capacitors, inductors, diodes, logic gates, multiplexers, buffers, modulators, demodulators, radios (e.g., transmit or receive radios or transceivers), sensors 1421 (e.g., a transducer that converts one form of energy (e.g., light, heat, electrical, mechanical, or other energy) to another form of energy), or the like, or a combination thereof), a main memory 1404 and a static memory 1406, which communicate with each other via a bus 1408. The machine 1400 (e.g., computer system) may further include a video display unit 1410 (e.g., a liquid crystal display (LCD) or a cathode ray tube (CRT)). The machine 1400 also includes an alphanumeric input device 1412 (e.g., a keyboard), a user interface (UI) navigation device 1414 (e.g., a mouse), a disk drive or mass storage unit 1416, a signal generation device 1418 (e.g., a speaker), and a network interface device 1420.

The disk drive or mass storage unit 1416 includes a machine-readable medium 1422 on which is stored one or more sets of data structures and instructions (e.g., software) 2024 embodying or utilized by any one or more of the methodologies or functions described herein. The instructions 1424 may also reside, completely or at least partially, within the main memory 1404 and/or within the processor 1402 during execution thereof by the machine 1400, the main memory 1404 and the processor 1402 also constituting machine-readable media.

The machine 1400 as illustrated includes an output controller 1426. The output controller 1426 manages data flow to/from the machine 1400. The output controller 1426 is sometimes called a device controller, with software that directly interacts with the output controller 1426 being called a device driver.

While the machine-readable medium 1422 is shown in an embodiment to be a single medium, the term "machine-readable medium" may include a single medium or multiple media (e.g., a centralized or distributed database, and/or associated caches and servers) that store the one or more instructions 1424 or data structures. The term "machine-readable medium" shall also be taken to include any tangible medium that is capable of storing, encoding, or carrying instructions for execution by the machine and that cause the machine to perform any one or more of the methodologies of the present disclosure, or that is capable of storing, encoding, or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), EEPROM, and flash memory devices; magnetic disks such as internal hard disks and removable disks; magneto-optical disks; and CD-ROM and DVD-ROM disks.

The instructions 1424 may further be transmitted or received over a communications network 1428 using a transmission medium. The instructions 1424 may be transmitted using the network interface device 1420 and any one of a number of well-known transfer protocols (e.g., HTTP). Examples of communication networks include a LAN, a WAN, the Internet, mobile telephone networks, Plain Old Telephone (POTS) networks, and wireless data networks (e.g., WiFi and WiMax networks). The term "transmission medium" shall be taken to include any intangible medium that is capable of storing, encoding, or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

ADDITIONAL NOTES

The above detailed description includes references to the accompanying drawings, which form a part of the detailed description. The drawings show, by way of illustration but not by way of limitation, specific embodiments in which the disclosure may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that elements after such a term (e.g., comprising, including, having) in a claim are still deemed to fall within the scope of that claim. Moreover, in the following claims, the terms "first," "second," and "third," and so forth, are used merely as labels, and are not intended to impose numerical requirements on their objects.

Embodiments of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions, or the specific components or modules illustrated in the figures and described herein. Other embodiments of the disclosure may include different computer-executable instructions or components having more or less functionality than illustrated and described herein.

Method examples (e.g., operations and functions) described herein may be machine or computer-implemented at least in part (e.g., implemented as software code or instructions). Some examples may include a computer-readable medium or machine-readable medium encoded with instructions operable to configure an electronic device to perform methods as described in the above examples. An implementation of such methods may include software code, such as microcode, assembly language code, a higher-level language code, or the like (e.g., "source code"). Such software code may include computer-readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CD-ROMS, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., ROMs), EPROMS, EEPROMS, or any type of media suitable for storing electronic instructions, and the like. Such computer-readable storage medium coupled to a computer system bus may be accessible by the processor and other parts of the OIS.

In an embodiment, the computer-readable storage medium may have encoded a data structure for a treatment planning, wherein the treatment plan may be adaptive. The data structure for the computer-readable storage medium may be at least one of a Digital Imaging and Communications in Medicine (DICOM) format, an extended DICOM format, an XML format, and the like. DICOM is an international communications standard that defines the format used to transfer medical image-related data between various types of medical equipment. DICOM RT refers to the communication standards that are specific to radiation therapy.

In various embodiments of the disclosure, the method of creating a component or module may be implemented in software, hardware, or a combination thereof. The methods provided by various embodiments of the present disclosure, for example, may be implemented in software by using standard programming languages such as, for example, Compute Unified Device Architecture (CUDA), C, C++, Java, Python, JavaScript and the like; and using standard machine learning/deep learning library (or API), such as tensorflow, torch and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface may be configured by providing configuration parameters and/or sending signals to prepare the communication interface to provide a data signal describing the software content. The communication interface may be accessed via one or more commands or signals sent to the communication interface.

The present disclosure also relates to a system for performing the operations herein. This system may be specially constructed for the required purposes, or it may comprise a general-purpose computer selectively activated or reconfigured by a computer program stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved, and other beneficial results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are example embodiments. Many other embodiments will be apparent to those of skill in the art upon reviewing the above description. The scope of the disclosure should, therefore, be determined with reference to the appended claims, along with the full scope of equivalents to which such claims are entitled. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

The claimed invention is:

1. A computer-implemented method for generating a radiotherapy treatment plan for a subject including training processing circuitry to automatically contour an image depicting an anatomy of the subject, the method comprising:

jointly training a first machine learning model and a second machine learning model by using images from a first training dataset and a second training dataset independent from the first training dataset, wherein the first machine learning model and the second machine learning model are configured to share at least one learned model parameter, and wherein, when trained, the machine learning models are configured to automatically contour images for radiotherapy treatment.

2. The method of claim 1, wherein jointly training the at least two machine learning models includes:

inputting the first training dataset of a first type to train a first one of the machine learning models, wherein each training sample from the first training dataset is a single image, wherein the first machine learning model is configured to use at least one first parameter and the shared learned model parameter, the at least one first parameter being a learned parameter specific to the first machine learning model and not trained by a second one of the machine learning models; and inputting a second training dataset of a second type to the second one of the machine learning models, wherein each training sample from the second training dataset comprises a single image, wherein the first type is different than the second type, wherein the second machine learning model is configured to use at least one second parameter and the shared learned model parameter, the at least one second parameter being a learned parameter specific to the second machine learning model and not trained by the first one of the machine learning models, and wherein the second machine learning model is coupled to the first machine learning model to share the parameter.

3. The method of claim 2, wherein the first machine learning model and the second machine learning model form part of a convolutional block of a convolutional neural network.

4. The method of claim 3, wherein the convolutional block includes a first normalization layer configured to receive data from the first training dataset and a second normalization layer configured to receive data from the second training dataset.

5. The method of claim 2, wherein the first type includes a T1-weighted image, and wherein the second type includes a T2-weighted image.

6. The method of claim 2, wherein the first type includes either a T1-weighted image or a T2-weighted image having a first scan time, and wherein the second type includes either a T1-weighted image or a T2-weighted image having a different time greater than the first scan time.

7. The method of claim 2, wherein the first type includes an anatomy of a male subject and the second type includes an anatomy of a female subject.

8. The method of claim 7, wherein the first type includes a male pelvic region and the second type includes female pelvic region.

9. The method of claim 2, wherein the first type includes a female subject having had an ablative surgery and the second type includes a female subject not having had the ablative surgery.

10. The method of claim 2, wherein the first type includes a male subject having had an ablative surgery and the second type includes a male subject not having had the ablative surgery.

11. A computer-implemented method for generating a radiotherapy treatment plan for a subject including automatically contouring an image depicting an anatomy of the subject, the method comprising:

obtaining the image of the subject;

selecting, based on an image parameter, a previously trained first machine learning model, wherein the previously trained first machine learning model was jointly trained with a second machine learning model by using images from a first training dataset and a second training dataset independent from the first training dataset;

applying the first previously trained machine learning model to the image of the subject to generate a machine learning model output, wherein applying includes applying a shared learned parameter learned during joint training with the second machine learning model, and a learned parameter specific to the first machine learning model and not shared with the second machine learning model;

contouring, without user intervention and based on the first machine learning model output, one or more anatomical structures of the image; and processing the one or more contoured anatomical structures to generate the radiotherapy treatment plan.

12. The method of claim 11, wherein the previously trained first machine learning model was trained using anatomies of male subjects and female subjects.

13. The method of claim 12, wherein the anatomies of male subjects and female subjects include anatomies of male pelvic regions and female pelvic regions.

14. The method of claim 11, wherein the previously trained first machine learning model was trained using anatomies of female subjects having had an ablative surgery and female subjects not having had the ablative surgery.

15. The method of claim 11, wherein the previously trained first machine learning model was trained using anatomies of male subjects having had an ablative surgery and male subjects not having had the ablative surgery.

16. The method of claim 11 wherein the previously trained first machine learning model was trained using images having different imaging contrasts.

17. The method of claim 11, wherein the previously trained first machine learning model was trained using T2-weighted images having a first scan time and T2-weighted images having a second scan time greater than the first time.

18. The method of claim 11, wherein the first machine learning model is configured to generate a different set of structures than the second machine learning model.

19. A radiotherapy system for generating a radiotherapy treatment plan for a subject including automatically contouring an image depicting an anatomy of the subject, the radiotherapy system comprising:

a radiation therapy device configured to deliver a dose of radiation to an anatomical region of interest; and a processor configured to:

obtain the image of the subject;

select, based on an image parameter, a previously trained first machine learning model, wherein the previously trained first machine learning model was jointly trained with a second machine learning model by using images from a first training dataset and a second training dataset independent from the first training dataset;

apply the first previously trained machine learning model to the image of the subject to generate a machine learning model output, wherein applying includes applying a shared learned parameter learned during joint training with the second machine learning model, and a learned parameter specific to the first machine learning model and not shared with the second machine learning model;

contour, without user intervention and based on the first machine learning model output, one or more anatomical structures of the image; and process the one or more contoured anatomical structures to generate the radiotherapy treatment plan.

20. The radiotherapy system of claim 19, wherein the previously trained first machine learning model was trained using images having different imaging contrasts.

21. The radiotherapy system of claim 19, wherein the previously trained first machine learning model was trained using T2-weighted images having a first scan time and T2-weighted images having a second scan time greater than the first scan time.

22. The radiotherapy system of claim 19, wherein the previously trained first machine learning model was trained using anatomies of male subjects and female subjects.

23. The radiotherapy system of claim 19, wherein the first machine learning model is configured to generate a different set of structures than the second machine learning model.

* * * * *